(12) United States Patent
Willms et al.

(10) Patent No.: US 8,912,124 B2
(45) Date of Patent: Dec. 16, 2014

(54) USE OF DERIVATIVES OF (1-CYANOCYCLOPROPYL) PHENYLPHOSPHINIC ACID, ESTERS THEREOF AND/OR SALTS THEREOF FOR ENHANCING TOLERANCE IN PLANTS TO ABIOTIC STRESS

(75) Inventors: Lothar Willms, Hofheim (DE); Hans-Joachim Zeiβ, Sulzbach (DE); Marco Busch, Burscheid-Ösinghausen (DE); Christopher Hugh Rosinger, Hofheim (DE); Ines Heinemann, Hofheim (DE); Isolde Häuser-Hahn, Leverkusen (DE); Martin Jeffrey Hills, Idstein (DE); Pascal Von Koskull-Döring, Frankfurt am Main (DE)

(73) Assignee: Bayer Cropscience AG, Frankfurt am Main (DE)

( * ) Notice: Subject to any disclaimer, the term of this patent is extended or adjusted under 35 U.S.C. 154(b) by 161 days.

(21) Appl. No.: 13/081,309

(22) Filed: Apr. 6, 2011

(65) Prior Publication Data

US 2011/0294664 A1   Dec. 1, 2011

Related U.S. Application Data

(60) Provisional application No. 61/322,364, filed on Apr. 9, 2010.

(30) Foreign Application Priority Data

Apr. 9, 2010   (EP) ..................... 10159470

(51) Int. Cl.
*A01N 57/22*   (2006.01)
*C07F 9/58*   (2006.01)
*C07F 9/30*   (2006.01)
*C07F 9/32*   (2006.01)

(52) U.S. Cl.
CPC ............... *A01N 57/22* (2013.01); *C07F 9/582* (2013.01); *C07F 9/304* (2013.01); *C07F 9/3229* (2013.01); *C07F 9/3264* (2013.01); *C07F 9/327* (2013.01); *C07F 9/3276* (2013.01); *C07F 9/3288* (2013.01)
USPC ........... 504/109; 504/127; 504/141; 504/194; 504/202; 514/75; 514/109; 514/112; 514/114; 514/142; 514/520; 514/576; 514/578; 514/646; 423/299; 423/302; 423/304; 558/70; 558/167; 558/303; 558/386; 558/389; 562/8; 562/11; 562/25; 568/8; 568/14; 568/17

(58) Field of Classification Search
USPC ........... 504/194, 202; 514/75, 109, 112, 114, 514/142, 520, 576, 578, 646; 423/299, 302, 423/304; 558/70, 167, 303, 386, 389; 562/8, 11, 25; 568/8, 14, 17
See application file for complete search history.

(56) References Cited

U.S. PATENT DOCUMENTS

| 4,339,443 A | 7/1982 | Baillie et al. |
| 5,276,268 A | 1/1994 | Strauch et al. |

FOREIGN PATENT DOCUMENTS

| CA | 1321364 | 1/1988 | | |
| EP | 0275957 | 1/1988 | | |
| GB | 2004889 | 4/1979 | | |
| GB | 2004889 A | 4/1979 | | |
| GB | 2214184 | 8/1989 | | |
| GB | 2214184 A | * 8/1989 | ............... | C07F 9/28 |

OTHER PUBLICATIONS

G. Hoerlein, Reviews of Environmental Contamination and Toxicology, 1994, pp. 73-145. vol. 138, Springer-Verlag, New York, NY.
Vinogradova et al., The Selective C-Mono-and C,C-Dialkylation of Thiophosphorylacetonitriles and Reacitivity of the Products, Phosphorus, Sulfur and Silicon, 1999, vol. 144-146, pp. 589-592. OPA(Overseas Publishers Association) N.V.
P.V. Kazakov et al., Cycloalkylation of Compounds in the Series of Phosphorus-Substituted Derivatives of Acetic Acid, Tanslated from Izvestiya Akademii Nauk SSSR, Seriya Khimicheskaya, No. 8,pp. 1873-1880, Aug. 1990, Original article Submitted Oct. 31, 1989.
Vingordova N.M. et al., "The selective C-mono- and C, C-dialkylation of thiophosphorylacetonitrles and reactivity of the products", Phosphorus, Sulfur and Silicon and the Related Elements, Jan. 1, 1999, pp. 589-592, Taylor & Francis, US.
Kazakov, P.V. et al., "Cycloalkylation of Compounds in the Series of Phosphorussubsituted Derivatives of Acetic Acid", Bulletin of the Academy of Sciences of the USSR Division of Chemical Sciences, Jan. 1, 1991, pp. 1702-1708, Plenum Publishing Corporation.

\* cited by examiner

*Primary Examiner* — Jane C Oswecki
(74) *Attorney, Agent, or Firm* — Frommer Lawrence & Haug LLP

(57) ABSTRACT

The invention relates to derivatives of (1-cyanocyclopropyl) phenylphosphinic acid of the formula (I)

(I)

[structure: phenyl ring with $(R^1)_n$ substituents, connected to P(=O)(OR$^2$)- group bonded to a cyclopropyl bearing a C≡N group]

and to salts thereof, of the formula (II), (II)

[structure: phenyl ring with $(R^1)_n$ substituents, connected to P(=O)(O$^-$)- group bonded to a cyclopropyl bearing a C≡N group, with $M^{z+}$ counterion, subscript z]

for enhancing stress tolerance in plants to abiotic stress, preferably to drought stress, especially for enhancing plant growth and/or for increasing plant yield.

11 Claims, No Drawings

USE OF DERIVATIVES OF (1-CYANOCYCLOPROPYL)PHENYLPHOSPHINIC ACID, ESTERS THEREOF AND/OR SALTS THEREOF FOR ENHANCING TOLERANCE IN PLANTS TO ABIOTIC STRESS

The invention relates to the use of derivatives of (1-cyanocyclopropyl)phenylphosphinic acid, esters thereof and salts thereof for enhancing stress tolerance in plants to abiotic stress, preferably to drought stress, especially for enhancing plant growth and/or for increasing plant yield, and to processes for preparing derivatives of (1-cyanocyclopropyl)phenylphosphinic acid, esters thereof and salts thereof.

It is known that specific aliphatic phosphinic acid derivatives, for example (RS)-2-amino-4-(hydroxymethylphosphinyl)butanoic acid (glufosinate), are used as a nonselective herbicide, or as a selective herbicide in genetically modified crop plants (G. Hörlein, Rev. Environ. Contam Toxicol., 138, (1994), 73-145; E. Strauch et al., EP 275957 (1988)).

It is also known that acetylmethylphosphinic acid, for example in the form of the sodium salt, has interesting herbicidal action (A. C. Baillie et al., U.S. Pat. No. 4,339,443 (1982)).

It is also known that cycloaliphatic phosphonic diesters, such as dibutyl 1-butylaminocyclohexylphosphonate (buminofos), can be used as herbicides and plant growth regulators (Farm Chemicals Handbook '91, Meister Publishing Company (1991), C53).

It is known that plants react to natural stress conditions, for example drought, cold, heat, aridity or lack of water (though dryness and lack of water similarly cause drought stress), injury, pathogenic attack (viruses, bacteria, fungi, insects), etc., but also to herbicides, with specific or unspecific defense mechanisms

[Pflanzenbiochemie (Plant Biochemistry), p. 393-462, Spektrum Akademischer Verlag, Heidelberg, Berlin, Oxford, Hans W. Heldt, 1996; Biochemistry and Molecular Biology of Plants, p. 1102-1203, American Society of Plant Physiologists, Rockville, Md., eds. Buchanan, Gruissem, Jones, 2000].

In plants, there is knowledge of numerous proteins, and the genes which code for them, which are involved in defense reactions to abiotic stress (for example cold, heat, drought, salt, flooding). Some of these form part of signal transduction chains (for example transcription factors, kinases, phosphatases) or cause a physiological response of the plant cell (for example ion transport, deactivation of reactive oxygen species). The signaling chain genes of the abiotic stress reaction include transcription factors of the DREB and CBF classes (Jaglo-Ottosen et al., 1998, Science 280: 104-106). The reaction to salinity stress involves phosphatases of the ATPK and MP2C types. In addition, in the event of salinity stress, the biosynthesis of osmolytes such as proline or sucrose is often activated. This involves, for example, sucrose synthase and proline transporters (Hasegawa et al., 2000, Annu Rev Plant Physiol Plant Mol Biol 51: 463-499). The stress defense of the plants to cold and drought uses some of the same molecular mechanisms. There is a known accumulation of what are called late embryogenesis abundant proteins (LEA proteins), which include the dehydrins as an important class (Ingram and Bartels, 1996, Annu Rev Plant Physiol Plant Mol Biol 47: 277-403, Close, 1997, Physiol Plant 100: 291-296). These are chaperones which stabilize vesicles, proteins and membrane structures in stressed plants (Bray, 1993, Plant Physiol 103: 1035-1040). In addition, there is frequently induction of aldehyde dehydrogenases, which deactivate the reactive oxygen species (ROS) which form in the event of oxidative stress (Kirch et al., 2005, Plant Mol Biol 57: 315-332).

Heat shock factors (HSF) and heat shock proteins (HSP) are activated in the event of heat stress and play a similar role here as chaperones to that of dehydrins in the event of cold and drought stress (Yu et al., 2005, Mol Cells 19: 328-333).

A number of plant-endogenous signaling substances involved in stress tolerance or pathogen defense are already known. Examples here include salicylic acid, benzoic acid, jasmonic acid or ethylene [Biochemistry and Molecular Biology of Plants, p. 850-929, American Society of Plant Physiologists, Rockville, Md., eds. Buchanan, Gruissem, Jones, 2000]. Some of these substances or the stable synthetic derivatives and derived structures thereof are also effective on external application to plants or in seed dressing, and activate defense reactions which cause elevated stress tolerance or pathogen tolerance of the plant [Sembdner, and Parthier, 1993, Ann. Rev. Plant Physiol. Plant Mol. Biol. 44: 569-589].

It is additionally known that chemical substances can increase the tolerance of plants to abiotic stress. Such substances are applied by seed dressing, by leaf spraying or by soil treatment. For instance, an increase in abiotic stress tolerance of crop plants by treatment with elicitors of systemic acquired resistance (SAR) or abscisic acid derivatives is described (Schading and Wei, WO-200028055, Abrams and Gusta, U.S. Pat. No. 5,201,931, Churchill et al., 1998, Plant Growth Regul 25: 35-45) or azibenzolar-S-methyl. Similar effects are also observed on application of fungicides, especially from the group of the strobilurins or of the succinate dehydrogenase inhibitors, and are frequently also accompanied by an increase in yield (Draber et al., DE-3534948, Bartlett et al., 2002, Pest Manag Sci 60: 309). It is likewise known that the herbicide glyphosate in low dosage stimulates the growth of some plant species (Cedergreen, Env. Pollution 2008, 156, 1099).

In addition, effects of growth regulators on the stress tolerance of crop plants have been described (Morrison and Andrews, 1992, J Plant Growth Regul 11: 113-117, RD-259027). In the event of osmotic stress, a protective effect has been observed as a result of application of osmolytes, for example glycine betaine or the biochemical precursors thereof, e.g. choline derivatives (Chen et al., 2000, Plant Cell Environ 23: 609-618, Bergmann et al., DE-4103253). The effect of antioxidants, for example naphthols and xanthines, to increase abiotic stress tolerance in plants has also already been described (Bergmann et al., DD-277832, Bergmann et al., DD-277835). However, the molecular causes of the anti-stress action of these substances are substantially unknown.

It is additionally known that the tolerance of plants to abiotic stress can be increased by a modification of the activity of endogenous poly-ADP-ribose polymerases (PARP) or poly-(ADP-ribose) glycohydrolases (PARG) (de Block et al., The Plant Journal, 2004, 41, 95; Levine et al., FEBS Lett. 1998, 440, 1; WO0004173; WO04090140).

It is thus known that plants possess several endogenous reaction mechanisms which can bring about effective defense against a wide variety of different harmful organisms and/or natural abiotic stress.

Since the environmental and economic demands on modern crop treatment compositions are increasing constantly, for example with respect to toxicity, selectivity, application rate, formation of residues and favorable manufacture, there is a constant need to develop novel crop treatment compositions which have advantages over those known, at least in some areas.

It was therefore an object of the present invention to provide further compounds which increase tolerance in plants to abiotic stress, preferably to drought stress.

The present invention accordingly provides for the use of derivatives of (1-cyanocyclopropyl)phenylphosphinic acid and esters thereof, of the formula (I)

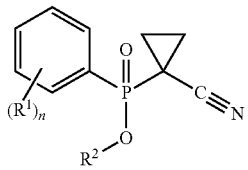

(I)

for increasing tolerance in plants with respect to abiotic stress, preferably to drought stress, where $R^1$ is halogen, branched or unbranched alkyl, cycloalkyl, alkenyl, alkynyl, aryl, arylalkyl, heteroaryl, heteroarylalkyl, alkoxyalkyl, hydroxyalkyl, alkoxyalkenyl, alkylthio, haloalkylthio, alkylsulfinyl, alkylsulfonyl, haloalkyl, alkoxy, haloalkoxy, carboxyl, alkoxycarbonyl, aminocarbonyl which is optionally mono- or disubstituted, cyano, amino or nitro, $R^2$ is hydrogen, branched or unbranched alkyl, cycloalkyl, cycloalkylalkyl, alkenyl, alkenylalkyl, alkynyl, alkynylalkyl, aryl, arylalkyl, heteroaryl, heteroarylalkyl, alkoxyalkyl, hydroxyalkyl, alkoxyalkenyl, hydroxyalkenyl, alkylthioalkyl, haloalkyl, alkylaminoalkyl, bisalkylaminoalkyl, cycloalkylaminoalkyl, and n is 0, 1, 2, 3, 4, 5.

Preference is given to the inventive use of derivatives of (1-cyanocyclopropyl)phenylphosphinic acid and esters thereof, of the formula (I), for increasing tolerance in plants to abiotic stress, in which $R^1$ is halogen, branched or unbranched alkyl, cycloalkyl, alkenyl, alkynyl, aryl, alkoxyalkyl, alkylthio, haloalkyl, alkoxy, carboxyl, alkoxycarbonyl, $R^2$ is hydrogen, branched or unbranched alkyl, cycloalkyl, alkenyl, alkynyl, arylalkyl, heteroaryl, heteroarylalkyl, alkoxyalkyl, hydroxyalkyl, hydroxyalkenyl, haloalkyl, and n is 0, 1, 2, 3, 4, 5.

Particular preference is given to the inventive use of derivatives of (1-cyanocyclopropyl)phenylphosphinic acid and esters thereof, of the formula (I), for increasing tolerance in plants to abiotic stress, in which $R^1$ is halogen, branched or unbranched $(C_1-C_6)$-alkyl, $(C_3-C_7)$-cycloalkyl, $(C_2-C_4)$-alkenyl, $(C_1-C_4)$-alkynyl, $(C_1-C_4)$-alkoxy-$(C_1-C_4)$-alkyl, $(C_1-C_4)$-alkylthio, halo-$(C_2-C_4)$-alkyl, $(C_1-C_4)$-alkoxy, carboxyl, $(C_1-C_4)$-alkoxycarbonyl, $R^2$ is hydrogen, branched or unbranched $(C_1-C_6)$-alkyl, $(C_3-C_7)$-cycloalkyl, $(C_2-C_6)$-alkenyl, $(C_2-C_6)$-alkynyl, $(C_1-C_4)$-alkoxy-$(C_1-C_4)$-alkyl, halo-$(C_1-C_6)$-alkyl and n is 0, 1, 2 or 3.

The present invention likewise provides for the inventive use of compounds of the formula (I) according to the aforementioned general, preferred and particularly preferred definitions for the $(R^1)_n$ radical, in which $R^2$ is hydrogen, and which form, as a result of addition of a suitable inorganic or organic base, salts of the formula (II)

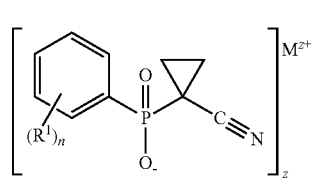

(II)

for increasing tolerance in plants with respect to abiotic stress, preferably to drought stress where the cation (M) of the formula (II) is (a) an ion of the alkali metals, preferably lithium, sodium, potassium, or (b) an ion of the alkaline earth metals, preferably calcium and magnesium, or (c) an ion of the transition metals, preferably manganese, copper, zinc and iron, or (d) an ammonium ion in which one, two, three or all four hydrogen atoms are optionally replaced by identical or different radicals from the group of $(C_1-C_4)$-alkyl, hydroxy-$(C_1-C_4)$-alkyl, $(C_3-C_6)$-cycloalkyl, $(C_1-C_4)$-alkoxy-$(C_1-C_4)$-alkyl, hydroxy-$(C_1-C_4)$-alkoxy-$(C_1-C_4)$-alkyl, $(C_1-C_6)$-mercaptoalkyl, phenyl or benzyl, where the aforementioned radicals are optionally substituted by one or more identical or different radicals from the group of halogen, such as F, Cl, Br or I, nitro, cyano, azido, $(C_1-C_6)$-alkyl, $(C_1-C_6)$-haloalkyl, $(C_3-C_6)$-cycloalkyl, $(C_1-C_6)$-alkoxy, $(C_1-C_6)$-haloalkoxy and phenyl, and where in each case two substituents on the nitrogen atom together optionally form an unsubstituted or substituted ring, or (e) a phosphonium ion, or (f) a sulfonium ion or sulfoxonium ion, preferably tri-$((C_1-C_4)$-alkyl)sulfonium or tri-$((C_1-C_4)$-alkyl)sulfoxonium, or (g) an oxonium ion, preferably tri-$((C_1-C_4)$-alkyl)oxonium, or (h) an optionally singly or multiply fused and/or $(C_1-C_4)$-alkyl-substituted saturated or unsaturated/aromatic N-containing heterocyclic ionic compound having 1-10 carbon atoms in the ring system, and z is 1, 2 or 3.

Preference is given to the inventive use of compounds of the formula (II) for increasing tolerance in plants to abiotic stress, where the cation (M) of the formula (II) is (a) an ion of the alkali metals, preferably lithium, sodium, potassium, or (b) an ion of the alkaline earth metals, preferably calcium and magnesium, or (c) an ion of the transition metals, preferably manganese, copper, zinc and iron, or (d) an ammonium ion in which one, two, three or all four hydrogen atoms are optionally replaced by identical or different radicals from the group of $(C_1-C_4)$-alkyl, hydroxy-$(C_1-C_4)$-alkyl, $(C_3-C_4)$-cycloalkyl, $(C_1-C_2)$-alkoxy-$(C_1-C_2)$-alkyl, hydroxy-$(C_1-C_2)$-alkoxy-$(C_1-C_2)$-alkyl, $(C_1-C_2)$-mercaptoalkyl, phenyl or benzyl, where the aforementioned radicals are optionally substituted by one or more identical or different radicals from the group of halogen, such as F, Cl, Br or I, nitro, cyano, azido, $(C_1-C_2)$-alkyl, $(C_1-C_2)$-haloalkyl, $(C_3-C_4)$-cycloalkyl, $(C_1-C_2)$-alkoxy, $(C_1-C_2)$-haloalkoxy and phenyl, and where in each case two substituents on the nitrogen atom together optionally form an unsubstituted or substituted ring, or (e) a quaternary phosphonium ion, preferably tetra-$((C_1-C_4)$-alkyl)phosphonium and tetraphenylphosphonium, where the (C$_1$-C$_4$)-alkyl radicals and the phenyl radicals are optionally mono- or polysubstituted by identical or different radicals from the group of halogen, such as F, Cl, Br or I, (C$_1$-C$_2$)-alkyl, (C$_1$-C$_2$)-haloalkyl, (C$_3$-C$_4$)-cycloalkyl, (C$_1$-C$_2$)-alkoxy and (C$_1$-C$_2$)-haloalkoxy, or (f) a tertiary sulfonium ion or sulfoxonium ion, preferably tri-((C$_1$-C$_4$)-alkyl)sulfonium or triphenylsulfonium, where the (C$_1$-C$_4$)-alkyl radicals and the phenyl radicals are optionally mono- or polysubstituted by identical or different radicals from the group of halogen, such as F, Cl, Br or I, (C$_1$-C$_2$)-alkyl, (C$_1$-C$_2$)-haloalkyl, (C$_3$-C$_4$)-cycloalkyl, (C$_1$-C$_2$)-alkoxy and (C$_1$-C$_2$)-haloalkoxy, or tri-((C$_1$-C$_4$)-alkyl)sulfoxonium, or (g) a tertiary oxonium ion, preferably tri-((C$_1$-C$_4$)-alkyl)oxonium, where the (C$_1$-C$_4$)-alkyl radicals are optionally mono- or polysubstituted by identical or different radicals from the group of halogen, such as F, Cl, Br or I, (C$_1$-C$_2$)-alkyl, (C$_1$-C$_2$)-haloalkyl, (C$_3$-C$_4$)-cycloalkyl, (C$_1$-C$_2$)-alkoxy and (C$_1$-C$_2$)-haloalkoxy, or (h) a cation from the group of the following heterocyclic compounds, for example pyridine, quinoline, 2-methylpyridine, 3-methylpyridine, 4-methylpyridine, 2,4-dimethylpyridine, 2,5-dimethylpyridine, 2,6-dimethylpyridine, 5-ethyl-2-methylpyridine, piperidine, pyrrolidine, morpholine, thiomorpholine, pyrrole, imidazole, 1,5-diazabicyclo[4.3.0]non-5-ene (DBN), 1,8-diazabicyclo[5.4.0]undec-7-ene (DBU), and z is 1, 2 or 3.

Particular preference is given to the inventive use of compounds of the formula (II) for increasing tolerance in plants to abiotic stress, in which the cation (M) is a sodium ion, a potassium ion, a lithium ion, a magnesium ion, a calcium ion, an NH$_4^+$ ion, a (2-hydroxyeth-1-yl)ammonium ion, a bis-N,N-(2-hydroxyeth-1-yl)ammonium ion, a tris-N,N,N-(2-hydroxyeth-1-yl)ammonium ion, a methylammonium ion, a dimethylammonium ion, a trimethylammonium ion, a tetramethylammonium ion, an ethylammonium ion, a diethylammonium ion, a triethylammonium ion, a tetraethylammonium ion, an isopropylammonium ion, a diisopropylammonium ion, a tetrapropylammonium ion, a tetrabutylammonium ion, a 2-(2-hydroxyeth-1-oxy)eth-1-ylammonium ion, a di(2-hydroxyeth-1-yl)ammonium ion, a trimethylbenzylammonium ion, a tri-((C$_1$-C$_4$)-alkyl)sulfonium ion or a tri-((C$_1$-C$_4$)-alkyl)oxonium ion, a benzylammonium ion, a 1-phenylethylammonium ion, a 2-phenylethylammonium ion, a diisopropylethylammonium ion, a pyridinium ion, a piperidinium ion, an imidazolium ion, a morpholinium ion, a 1,8-diazabicyclo[5.4.0]undec-7-enium ion, and z is 1 or 2.

Particular preference is further given to the inventive use of compounds of the formula (II) for increasing tolerance in plants to abiotic stress, in which the cation (M) is a sodium ion, a potassium ion, a magnesium ion, a calcium ion, an NH$_4^+$ ion or an isopropylammonium ion, and z is 1 or 2.

Very particular preference is given to the use of compounds of the formula (II) for increasing tolerance in plants to abiotic stress, in which the cation (M) is an isopropylammonium ion and z is 1.

With regard to the compounds of the formulae (I) and (II) specified in accordance with the invention and the precursors thereof, the terms used above and below are elucidated. These are familiar to the person skilled in the art and especially have the definitions elucidated hereinafter:

The term "halogen" means, for example, fluorine, chlorine, bromine or iodine. When the term is used for a radical, "halogen" means, for example, a fluorine, chlorine, bromine or iodine atom.

Alkyl means a straight-chain or branched open-chain, saturated hydrocarbyl radical which has optionally been mono- or polysubstituted. Preferred substituents are halogen atoms, alkoxy groups, haloalkoxy groups, cyano groups, alkylthio groups, haloalkylthio groups or nitro groups, particular preference being given to fluorine, chlorine, bromine or iodine.

"Haloalkyl", "-alkenyl" and "-alkynyl" mean, respectively, alkyl, alkenyl and alkynyl partly or fully substituted by identical or different halogen atoms, e.g. monohaloalkyl, for example $CH_2CH_2Cl$, $CH_2CH_2Br$, $CHClCH_3$, $CH_2Cl$, $CH_2F$; perhaloalkyl, for example $CCl_3$, $CClF_2$, $CFCl_2$, $CF_2CClF_2$, $CF_2CClFCF_3$; polyhaloalkyl, for example $CH_2CHFCl$, $CF_2CClFH$, $CF_2CBrFH$, $CH_2CF_3$; the term "perhaloalkyl" also includes the term "perfluoroalkyl", and the term "polyhaloalkyl" also includes the terms "partly fluorinated alkyl" and "partly fluorinated haloalkyl".

Haloalkoxy is, for example, $OCF_3$, $OCHF_2$, $OCH_2F$, $OCF_2CF_3$, $OCH_2CF_3$ and $OCH_2CH_2Cl$; the situation is equivalent for haloalkenyl and other halogen-substituted radicals.

The expression "(C$_1$-C$_4$)-alkyl" is a brief notation for alkyl having one to four carbon atoms according to the range stated for carbon atoms, i.e. comprises the methyl, ethyl, 1-propyl, 2-propyl, 1-butyl, 2-butyl, 2-methylpropyl or tert-butyl radicals. General alkyl radicals with a larger specified range of carbon atoms, e.g. "(C$_1$-C$_6$)-alkyl", correspondingly also encompass straight-chain or branched alkyl radicals with a greater number of carbon atoms, i.e. according to the example also the alkyl radicals having 5 and 6 carbon atoms.

Unless stated specifically, in the case of the hydrocarbyl radicals such as alkyl, alkenyl and alkynyl radicals, including in combined radicals, the lower carbon skeletons, for example having 1 to 6 carbon atoms, or in the case of unsaturated groups having 2 to 6 carbon atoms, are preferred. Alkyl radicals, including in the combined radicals such as alkoxy, haloalkyl, etc., mean, for example, methyl, ethyl, n- or i-propyl, n-, i-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals are defined as the possible unsaturated radicals corresponding to the alkyl radicals, where at least one double bond or triple bond is present. Preference is given to radicals having one double bond or triple bond.

Alkenyl especially also includes straight-chain or branched open-chain hydrocarbon radicals having more than one double bond, such as 1,3-butadienyl and 1,4-pentadienyl, but also allenyl or cumulenyl radicals having one or more cumulated double bonds, for example allenyl (1,2-propadienyl), 1,2-butadienyl and 1,2,3-pentatrienyl. Alkenyl means, for example, vinyl which may optionally be substituted by further alkyl radicals, for example prop-1-en-1-yl, but-1-en-1-yl, allyl, 1-methylprop-2-en-1-yl, 2-methylprop-2-en-1-yl, but-2-en-1-yl, 1-methylbut-3-en-1-yl and 1-methylbut-2-en-1-yl, 2-methylprop-1-en-1-yl, 1-methylprop-1-en-1-yl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl, pentenyl, 2-methylpentenyl or hexenyl.

Alkynyl especially also includes straight-chain or branched open-chain hydrocarbon radicals having more than one triple bond, or else having one or more triple bonds and one or more double bonds, for example 3-penten-1-yn-1-yl. (C$_2$-C$_6$)-Alkynyl means, for example, ethynyl, propargyl, 1-methylprop-2-yn-1-yl, 2-butynyl, 2-pentynyl or 2-hexynyl, preferably propargyl, but-2-yn-1-yl, but-3-yn-1-yl or 1-methylbut-3-yn-1-yl.

The term "cycloalkyl" means a carbocyclic, saturated ring system having preferably 3-8 ring carbon atoms, e.g. cyclopropyl, cyclobutyl, cyclopentyl or cyclohexyl. In the case of optionally substituted cycloalkyl, cyclic systems with substituents are included, also including substituents with a double bond on the cycloalkyl radical, for example an alkylidene group such as methylidene. In the case of optionally substituted cycloalkyl, polycyclic aliphatic systems are also included, for example bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, bicyclo[2.2.1]hept-2-yl(norbornyl), bicyclo[2.2.2]octan-2-yl, adamantan-1-yl and adamantan-2-yl. The expression "($C_3$-$C_7$)-cycloalkyl" means a brief notation for cycloalkyl having three to 7 carbon atoms corresponding to the range specified for carbon atoms.

In the case of substituted cycloalkyl, spirocyclic aliphatic systems are also included, for example spiro[2.2]pent-1-yl, spiro[2.3]hex-1-yl, spiro[2.3]hex-4-yl, 3-spiro[2.3]hex-5-yl.

Cycloalkenyl means a carbocyclic, nonaromatic, partially unsaturated ring system having preferably 4-8 carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl, also including substituents with a double bond on the cycloalkenyl radical, for example an alkylidene group such as methylidene. In the case of optionally substituted cycloalkenyl, the elucidations for substituted cycloalkyl apply correspondingly.

The term "aryl" means a mono-, bi- or polycyclic aromatic system having preferably 6 to 14, especially 6 to 10, ring carbon atoms, for example phenyl, naphthyl, anthryl, phenanthrenyl and the like, preferably phenyl.

The term "optionally substituted aryl" also includes polycyclic systems, such as tetrahydronaphthyl, indenyl, indanyl, fluorenyl, biphenylyl, where the bonding site is on the aromatic system.

In systematic terms, "aryl" is generally also encompassed by the term "optionally substituted phenyl".

According to the invention, the expression "heteroaryl" represents heteroaromatic compounds, i.e. fully unsaturated aromatic heterocyclic compounds, preferably 5- to 7-membered rings having 1 to 3, preferably 1 or 2, identical or different heteroatoms, preferably O, S or N. Inventive heteroaryls are, for example, furyl, thienyl, pyrazolyl, imidazolyl, 1,2,3- and 1,2,4-triazolyl, isoxazolyl, thiazolyl, isothiazolyl, 1,2,3-, 1,3,4-, 1,2,4- and 1,2,5-oxadiazolyl, azepinyl, pyrrolyl, pyridyl, pyridazinyl, pyrimidinyl, pyrazinyl, 1,3,5-, 1,2,4- and 1,2,3-triazinyl, 1,2,4-, 1,3,2-, 1,3,6- and 1,2,6-oxazinyl, oxepinyl, thiepinyl, 1,2,4-triazolonyl and 1,2,4-diazepinyl. The inventive heteroaryl groups may also be substituted by one or more identical or different radicals.

Alkoxy means an alkyl radical bonded via an oxygen atom, alkenyloxy means an alkenyl radical bonded via an oxygen atom, alkynyloxy means an alkynyl radical bonded via an oxygen atom, cycloalkyloxy means a cycloalkyl radical bonded via an oxygen atom and cycloalkenyloxy means a cycloalkenyl radical bonded via an oxygen atom.

According to the invention, "alkylthio"—alone or as a constituent of a chemical group—represents straight-chain or branched S-alkyl, preferably having 1 to 8 or having 1 to 6 carbon atoms, for example methylthio, ethylthio, n-propylthio, isopropylthio, n-butylthio, isobutylthio, sec-butylthio and tert-butylthio. Alkenylthio is an alkenyl radical bonded via a sulfur atom, alkynylthio is an alkynyl radical bonded via a sulfur atom, cycloalkylthio is a cycloalkyl radical bonded via a sulfur atom, and cycloalkenylthio is a cycloalkenyl radical bonded via a sulfur atom.

According to the invention, "alkylsulfinyl"—alone or as part of a chemical group—is straight-chain or branched alkylsulfinyl, preferably having 1 to 8 or having 1 to 6 carbon atoms, for example methylsulfinyl, ethylsulfinyl, n-propylsulfinyl, isopropylsulfinyl, n-butylsulfinyl, Isobutylsulfinyl, sec-butylsulfinyl and tert-butylsulfinyl.

According to the invention, "alkylsulfonyl"—alone or as part of a chemical group—represents straight-chain or branched alkylsulfonyl, preferably having 1 to 8 or having 1 to 6 carbon atoms, for example methylsulfonyl, ethylsulfonyl, n-propylsulfonyl, isopropylsulfonyl, n-butylsulfonyl, isobutylsulfonyl, sec-butylsulfonyl and tert-butylsulfonyl.

According to the invention, "cycloalkylsulfonyl"—alone or as part of a chemical group—represents optionally substituted cycloalkylsulfonyl, preferably having 3 to 6 carbon atoms, for example cyclopropylsulfonyl, cyclobutylsulfonyl, cyclopentylsulfonyl or cyclohexylsulfonyl.

According to the invention, "arylsulfonyl" is optionally substituted phenylsulfonyl or optionally substituted polycyclic arylsulfonyl, for example substituted by halogen, alkyl, haloalkyl, haloalkoxy or alkoxy groups.

According to the nature and the bonding of the substituents, the compounds of the formulae (I) and (II) may be present as stereoisomers. The possible stereoisomers defined by the specific three-dimensional form thereof, such as enantiomers, diastereomers, Z and E isomers, are all encompassed by the formulae (I) and (II). When, for example, one or more alkenyl groups are present, Z and E isomers may occur. When, for example, one or more asymmetric carbon, sulfur or phosphorus atoms are present, enantiomers and diastereomers may occur. Stereoisomers can be obtained from the mixtures obtained in the preparation by customary separation methods. The chromatographic separation can be effected either on the analytical scale to find the enantiomeric excess or the diastereomeric excess, or on the preparative scale to prepare test specimens for biological testing. It is equally possible to selectively prepare stereoisomers by using stereoselective reactions using optically active starting materials and/or auxiliaries. The invention thus also relates to all stereoisomers which are embraced by the formulae (I) and (II) but are not shown in their specific stereomeric form, and to mixtures thereof.

The radical definitions stated above, in general terms or listed within areas of preference, apply both to the end products of the formulae (I) and (II) and correspondingly to the starting materials or the intermediates required for the preparation in each case. These radical definitions can be exchanged with one another, i.e. including combinations between the preferred ranges stated.

The term "useful plants" as used here refers to crop plants which are employed as plants for obtaining foods, animal feeds or for industrial purposes.

The inventive derivatives of (1-cyanocyclopropyl)phenylphosphinic acid and esters thereof, of the formula (I), and the salts thereof, of the formula (II), have not been described before in the prior art; only ethyl (1-cyanocyclopropyl)phenylphosphinate (example No. 2-2 in table 2) can be obtained commercially (Ryan Scientific Screening Library, CAS No: 329267-42-7, Order No. T0504-4843).

The present invention therefore also provides derivatives of (1-cyanocyclopropyl)phenylphosphinic acid and esters thereof, of the formula (I),

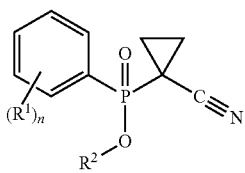
(I)

where
R¹ is halogen, branched or unbranched alkyl, cycloalkyl, alkenyl, alkynyl, aryl, arylalkyl, heteroaryl, heteroarylalkyl, alkoxyalkyl, hydroxyalkyl, alkoxyalkenyl, alkylthio, haloalkylthio, alkylsulfinyl, alkylsulfonyl, haloalkyl, alkoxy, haloalkoxy, carboxyl, alkoxycarbonyl, aminocarbonyl which is optionally mono- or disubstituted, cyano, amino or nitro,
R² is hydrogen, branched or unbranched alkyl, cycloalkyl, cycloalkylalkyl, alkenyl, alkenylalkyl, alkynyl, alkynylalkyl, aryl, arylalkyl, heteroaryl, heteroarylalkyl, alkoxyalkyl, hydroxyalkyl, alkoxyalkenyl, hydroxyalkenyl, alkylthioalkyl, haloalkyl, alkylaminoalkyl, bisalkylaminoalkyl, cycloalkylaminoalkyl, and
n is 0, 1, 2, 3, 4, 5,
excluding ethyl (1-cyanocyclopropyl)phenylphosphinate, and
salts of the formula (II)

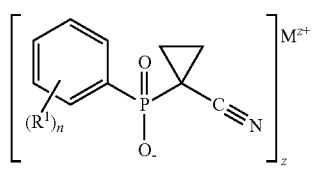
(II)

where
R¹ is halogen, branched or unbranched alkyl, cycloalkyl, alkenyl, alkynyl, aryl, arylalkyl, heteroaryl, heteroarylalkyl, alkoxyalkyl, hydroxyalkyl, alkoxyalkenyl, alkylthio, haloalkylthio, alkylsulfinyl, alkylsulfonyl, haloalkyl, alkoxy, haloalkoxy, carboxyl, alkoxycarbonyl, aminocarbonyl which is optionally mono- or disubstituted, cyano, amino or nitro,
n is 1, 2, 3, 4 or 5,
the cation (M) is
(a) an ion of the alkali metals, preferably lithium, sodium, potassium, or
(b) an ion of the alkaline earth metals, preferably calcium and magnesium, or
(c) an ion of the transition metals, preferably manganese, copper, zinc and iron, or
(d) an ammonium ion in which one, two, three or all four hydrogen atoms are optionally replaced by identical or different radicals from the group of $(C_1-C_4)$-alkyl, hydroxy-$(C_1-C_4)$-alkyl, $(C_3-C_6)$-cycloalkyl, $(C_1-C_4)$-alkoxy-$(C_1-C_4)$-alkyl, hydroxy-$(C_1-C_4)$-alkoxy-$(C_1-C_4)$-alkyl, $(C_1-C_6)$-mercaptoalkyl, phenyl or benzyl, where the aforementioned radicals are optionally substituted by one or more identical or different radicals from the group of halogen, such as F, Cl, Br or I, nitro, cyano, azido, $(C_1-C_6)$-alkyl, $(C_1-C_6)$-haloalkyl, $(C_3-C_6)$-cycloalkyl, $(C_1-C_6)$-alkoxy, $(C_1-C_6)$-haloalkoxy and phenyl, and where in each case two substituents on the nitrogen atom together optionally form an unsubstituted or substituted ring, or
(e) a phosphonium ion, or
(f) a sulfonium ion or sulfoxonium ion, preferably tri-$((C_1-C_4)$-alkyl)sulfonium or tri-$((C_1-C_4)$-alkyl)sulfoxonium, or
(g) an oxonium ion, preferably tri-$((C_1-C_4)$-alkyl)oxonium, or
(h) an optionally singly or multiply fused and/or $(C_1-C_4)$-alkyl-substituted saturated or unsaturated/aromatic N-containing heterocyclic ionic compound having 1-10 carbon atoms in the ring system,
and z is 1, 2 or 3.

The preparation and the use of the inventive compounds is illustrated by the examples which follow.

Various preparation routes for formation of the inventive compounds were used (see schemes 1 to 4 below). Selected detailed synthesis examples are detailed in the next section. The synthesis routes used and examined proceed from phosphorus-containing reactants which are commercially available or easily preparable by literature methods (see, for example, Houben-Weyl, Methoden der Organischen Chemie [Methods of Organic Chemistry], volumne XII/1 (1963), 324-331)

Scheme 1

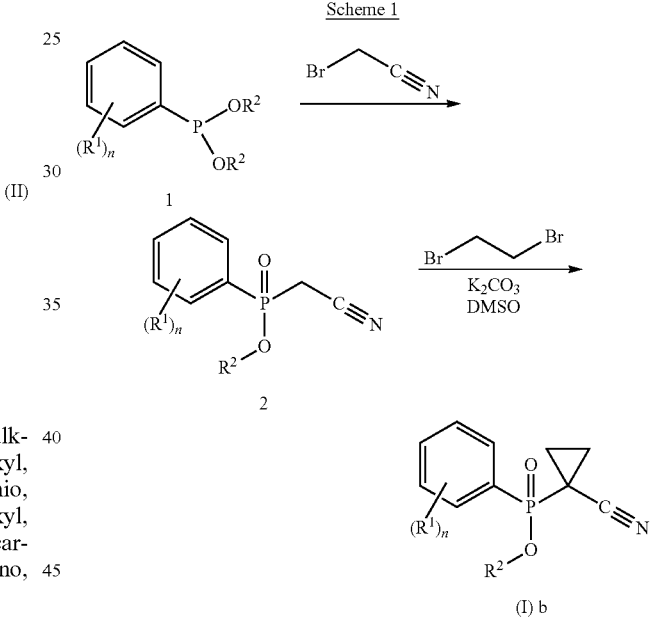

The optionally substituted phenyl dialkylphosphite (1) in question is converted by reaction with bromoacetonitrile to the corresponding optionally substituted (cyanomethyl)phenylphosphinic ester (2), which is cyclized with 1,2-dibromoethane in a suitable solvent, for example DMF or DMSO, to give an optionally substituted (1-cyanocyclopropyl)phenylphosphinic ester (I)b (scheme 1), where the $(R^1)_n$ and $R^2$ radicals are each as defined above for the formula (I).

Similar reactions with cyanomethyl-substituted phosphonic esters or phosphine oxides are described in the literature. For example, reaction of diethyl cyanomethylphosphonate with 1,2-dibromoethane and potassium carbonate gives diethyl 1-cyanocyclopropylphosphonate (J. Nasser, Phosphorus, Sulfur and Silicon and the Related Elements (1990), Vol. 54, 171-179), and reaction of ethyl(cyanomethyl)methylphosphinate with 1,2-dibromoethane and potassium carbonate gives ethyl (1-cyanocyclopropyl)methylphosphinate (P. V. Kazakov et al., Bulletin of the Academy of Sciences of the USSR, Vol. 39 (1990), 1702-1708).

The phosphinic esters (I)b thus obtained can be converted in the next step by cleavage with bromotrimethylsilane to the corresponding free phosphinic acids (I)a, which are in turn converted by reaction with a base to the corresponding salts, of the formula (II), of the parent phosphinic acids (scheme 2).

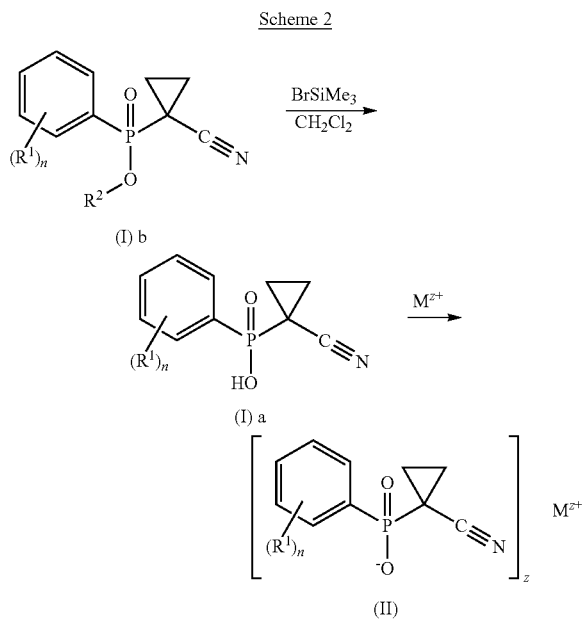

Scheme 2

(I) b (I) a (II)

Alternatively, the phosphinic acids (I)a obtained as intermediates can be reacted with a further hydroxyl compound, for example an optionally substituted alcohol or a hydroxyl heterocycle, to give further inventive compounds (I)b (scheme 3):

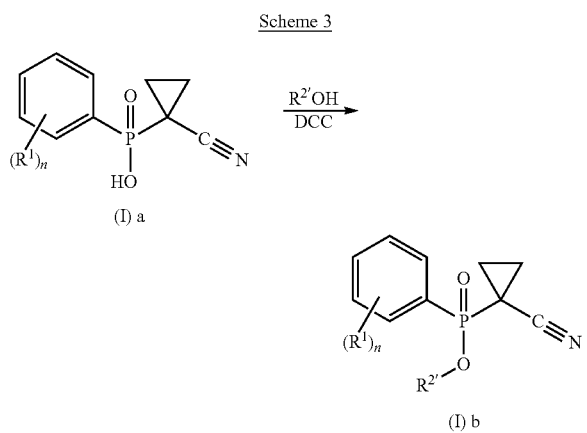

Scheme 3

(I) a (I) b

A further reaction route is that of the reaction of an optionally substituted phenylphosphite with a bromo- or chloroacetic ester, wherein the optionally substituted (alkoxycarbonylmethyl)phenylphosphinic esters (3) which form, in which the $(R^1)_n$ and $R^2$ radicals are each as defined for the formula (I) and $R^3$ is $(C_1-C_6)$-alkyl, are for their part first cyclized with 1,2-dibromoethane to give (4) in which $(R^1)_n$ and $R^2$ are each as defined for the formula (I) and $R_3$ is $(C_1-C_6)$-alkyl, and then converted with ammonia to the corresponding amides (5) in which $(R^1)_n$ and $R^2$ are each as defined for the formula (I), which are in turn converted by dehydration, for example with thionyl chloride, in a suitable aprotic solvent, to the inventive compounds (scheme 4).

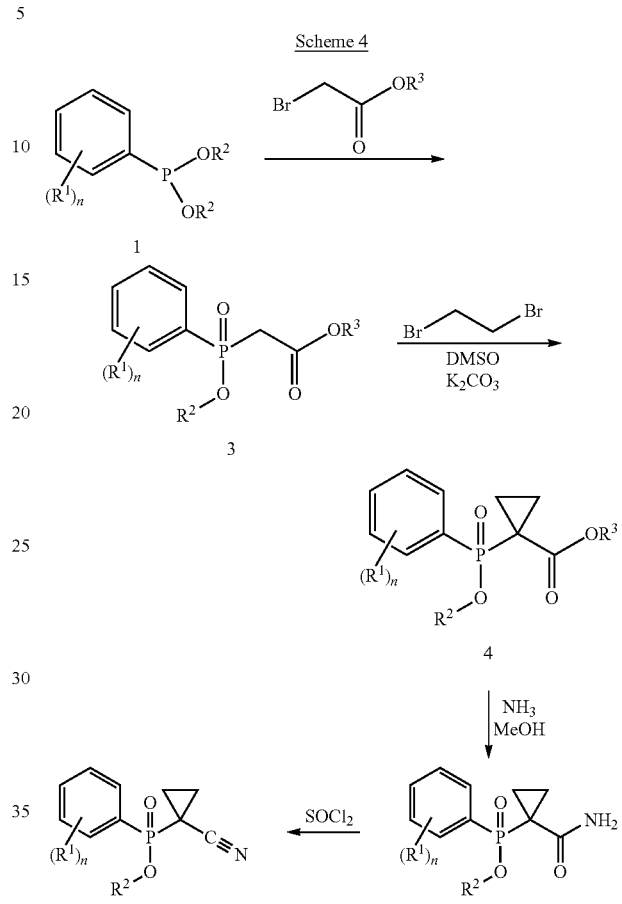

Scheme 4

1

3

4

5

(I) b

The $^1$H NMR spectroscopy data reported for the chemical examples described in the paragraphs which follow were obtained with a Bruker instrument (400 MHz, solvent: $CDCl_3$, $D_2O$, $CD_3OD$ or $d_6$-DMSO, internal standard: tetramethylsilane $\delta=0.00$ ppm), and the signals identified are defined as follows: br=broad; s=singlet, d=doublet, t=triplet, dd=double doublet, ddd=doublet of a double doublet, m=multiplet, q=quartet, quint=quintet, sext=sextet, sept=septet, dq=double quartet, dt=double triplet.

SYNTHESIS EXAMPLES

Ethyl(1-cyancyclopropyl)(4-fluorophenyl)phosphinate

Table Example: 2-5 a) Ethyl(cyanomethyl)(4-fluorophenyl)phosphinate 0.550 g (2.54 mmol) of 4-fluorophenyl diethylphosphite was initially charged at room temperature under argon, then 0.305 g of bromoacetonitrile was added dropwise. In the course of this, the internal temperature rose to 50° C. Subsequently, the reaction mixture was heated to 90° C. for 3 h and the bromoethane which formed was distilled off. After the reaction, the product was taken up in dichloromethane, washed with saturated NaCl solution and, after concentration, dried under high vacuum. This gave 0.573 g (81.2% of theory) of ethyl(cyanomethyl)(4-fluorophenyl)phosphinate.

$^1$H NMR (CDCl$_3$, 400 MHz) δ 7.88-8.0 (m, 2H) 7.23-7.30 (m, 2H) 4.05-4.31 (m, 2H) 2.85-3.12 (m, 2H) 1.87-1.95 (t, 3H).

b) Ethyl(1-cyanocyclopropyl)(4-fluorophenyl)phosphinate 0.470 g of ethyl(cyanomethyl)(4-fluorophenyl)phosphinate was initially charged in 20 ml of DMSO, and 0.572 g (4.138 mmol) of potassium carbonate and then 0.388 g of 1,2-dibromoethane were added. The mixture was stirred at room temperature for 4 h and then at 50° C. for 2 h. The reaction mixture was concentrated, taken up in dichloromethane and washed with H$_2$O.

The resulting crude product was purified by column chromatography. This gave 0.411 g (46.3%) of ethyl (1-cyanocyclopropyl)(4-fluorophenyl)phosphinate.

$^1$H NMR (CDCl$_3$, 400 MHz).

(4-Chlorophenyl)(1-cyanocyclopropyl)phosphinic acid

Table Example: 1-7

0.150 g (0.556 mmol) of ethyl (4-chlorophenyl)(1-cyanocyclopropyl)phosphinate was dissolved in 20 ml of chloroform, and 0.511 g (3.337 mmol) of bromotrimethylsilane was added. After stirring at room temperature for 18 hours, the solvent was removed, the residue was taken up in water and the solution was concentrated again by rotary evaporation. After column chromatography, 0.150 g (94.9% of theory) of (4-chlorophenyl)(1-cyanocyclopropyl)phosphinic acid was obtained.

$^1$H NMR (CDCl$_3$, 400 MHz): 7.7-7.8 (m, 2H) 7.42-7.50 (m, 2H) 1.40-1.60 (m, 4H)

(1-Cyanocyclopropyl)(4-fluorophenyl)phosphinic acid isopropylammonium salt

Table Example: 3-5

0.100 g (0.444 mmol) of (1-cyanocyclopropyl)(4-fluorophenyl)phosphinic acid was dissolved in 15 ml of dichloromethane, and 0.131 g (2.221 mmol) of isopropylamine was added. The solution was concentrated using a rotary evaporator and dried under high vacuum.

This gave 0.120 g (93.2% of theory) of (1-cyanocyclopropyl)(4-fluorophenyl)phosphinic acid isopropylammonium salt.

$^1$H NMR (CDCl$_3$, 400 MHz): 7.79-7.88 (m, 2H) 7.2-7.3 (m, 2H) 3.1-3.2 (m, 1H) 1.2-1.35 (m, 4H) 1.23 (d, 6H)

In analogy to the preparation examples cited and taking account of the general information regarding the preparation of the derivatives of (1-cyanocyclopropyl)phenylphosphinic acid of the formula (I), the following compounds are likewise obtained.

TABLE 1

(1-cyanocyclopropyl)phenylphosphinic acid derivatives of the formula (I) a

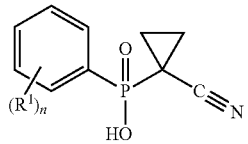

(I) a

| No. | R$^1$ | n |
|---|---|---|
| 1-1 | H | 1 |
| 1-2 | 2-F | 1 |
| 1-3 | 3-F | 1 |
| 1-4 | 4-F | 1 |
| 1-5 | 2-Cl | 1 |
| 1-6 | 3-Cl | 1 |
| 1-7 | 4-Cl | 1 |
| 1-8 | 2-Br | 1 |
| 1-9 | 3-Br | 1 |
| 1-10 | 4-Br | 1 |
| 1-11 | 2-I | 1 |
| 1-12 | 3-I | 1 |
| 1-13 | 4-I | 1 |
| 1-14 | 2-Me | 1 |
| 1-15 | 3-Me | 1 |
| 1-16 | 4-Me | 1 |
| 1-17 | 2-OMe | 1 |
| 1-18 | 3-OMe | 1 |
| 1-19 | 4-OMe | 1 |
| 1-20 | 2-CF$_3$ | 1 |
| 1-21 | 3-CF$_3$ | 1 |
| 1-22 | 4-CF$_3$ | 1 |
| 1-23 | 2-Et | 1 |
| 1-24 | 3-Et | 1 |
| 1-25 | 4-Et | 1 |
| 1-26 | 2-OEt | 1 |
| 1-27 | 3-OEt | 1 |
| 1-28 | 4-OEt | 1 |
| 1-29 | 2-CN | 1 |
| 1-30 | 3-CN | 1 |
| 1-31 | 4-CN | 1 |
| 1-32 | 2-COOMe | 1 |
| 1-33 | 3-COOMe | 1 |
| 1-34 | 4-COOMe | 1 |
| 1-35 | 2-COOEt | 1 |
| 1-36 | 3-COOEt | 1 |
| 1-37 | 4-COOEt | 1 |
| 1-38 | 2-SMe | 1 |
| 1-39 | 3-SMe | 1 |
| 1-40 | 4-SMe | 1 |
| 1-41 | 2-SOMe | 1 |
| 1-42 | 3-SOMe | 1 |
| 1-43 | 4-SOMe | 1 |
| 1-44 | 2-SO$_2$Me | 1 |
| 1-45 | 3-SO$_2$Me | 1 |
| 1-46 | 4-SO$_2$Me | 1 |
| 1-47 | 2-SEt | 1 |
| 1-48 | 3-SEt | 1 |
| 1-49 | 4-SEt | 1 |
| 1-50 | 2-SO$_2$Et | 1 |
| 1-51 | 3-SO$_2$Et | 1 |
| 1-52 | 4-SO$_2$Et | 1 |
| 1-53 | 2-CH$_2$OMe | 1 |
| 1-54 | 3-CH$_2$OMe | 1 |
| 1-55 | 4-CH$_2$OMe | 1 |
| 1-56 | 2-CH$_2$OEt | 1 |
| 1-57 | 3-CH$_2$OEt | 1 |
| 1-58 | 4-CH$_2$OEt | 1 |
| 1-59 | 2-CH$_2$SMe | 1 |
| 1-60 | 3-CH$_2$SMe | 1 |
| 1-61 | 4-CH$_2$SMe | 1 |
| 1-62 | 2-CH$_2$SEt | 1 |
| 1-63 | 3-CH$_2$SEt | 1 |
| 1-64 | 4-CH$_2$SEt | 1 |
| 1-65 | 2-allyl | 1 |
| 1-66 | 3-allyl | 1 |

TABLE 1-continued (1-cyanocyclopropyl)phenylphosphinic acid derivatives of the formula (I) a

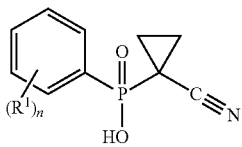

(I) a

| No. | R¹ | n |
|---|---|---|
| 1-67 | 4-allyl | 1 |
| 1-68 | 2-propargyl | 1 |
| 1-69 | 3-propargyl | 1 |
| 1-70 | 4-propargyl | 1 |
| 1-71 | 2-isopropyl | 1 |
| 1-72 | 3-isopropyl | 1 |
| 1-73 | 4-isopropyl | 1 |
| 1-74 | 2-cyclopropyl | 1 |
| 1-75 | 3-cyclopropyl | 1 |
| 1-76 | 4-cyclopropyl | 1 |
| 1-77 | 2-phenyl | 1 |
| 1-78 | 3-phenyl | 1 |
| 1-79 | 4-phenyl | 1 |
| 1-80 | 2-methoxyethyl | 1 |
| 1-81 | 3-methoxyethyl | 1 |
| 1-82 | 4-methoxyethyl | 1 |
| 1-83 | 2-OH | 1 |
| 1-84 | 3-OH | 1 |
| 1-85 | 4-OH | 1 |
| 1-86 | 2-$NO_2$ | 1 |
| 1-87 | 3-$NO_2$ | 1 |
| 1-88 | 4-$NO_2$ | 1 |
| 1-89 | 2-$NH_2$ | 1 |
| 1-90 | 3-$NH_2$ | 1 |
| 1-91 | 4-$NH_2$ | 1 |
| 1-92 | 2-$Me_2N$ | 1 |
| 1-93 | 3-$Me_2N$ | 1 |
| 1-94 | 4-$Me_2N$ | 1 |
| 1-95 | 2-$CONH_2$ | 1 |
| 1-96 | 3-$CONH_2$ | 1 |
| 1-97 | 4-$CONH_2$ | 1 |
| 1-98 | 2-$CONMe_2$ | 1 |
| 1-99 | 3-$CONMe_2$ | 1 |
| 1-100 | 4-$CONMe_2$ | 1 |
| 1-101 | 2,6-difluoro | 2 |
| 1-102 | 2,5-difluoro | 2 |
| 1-103 | 2,4-difluoro | 2 |
| 1-104 | 2,3-difluoro | 2 |
| 1-105 | 2,6-dichloro | 2 |
| 1-106 | 2,5-dichloro | 2 |
| 1-107 | 2,4-dichloro | 2 |
| 1-108 | 2,3-dichloro | 2 |
| 1-109 | 3,4-dichloro | 2 |
| 1-110 | 3,5-dichloro | 2 |
| 1-111 | 2,6-dimethyl | 2 |
| 1-112 | 2,5-dimethyl | 2 |
| 1-113 | 2,4-dimethyl | 2 |
| 1-114 | 2,3-dimethyl | 2 |
| 1-115 | 3,4-dimethyl | 2 |
| 1-116 | 3,5-dimethyl | 2 |
| 1-117 | 2,6-dimethoxy | 2 |
| 1-118 | 2,5-dimethoxy | 2 |
| 1-119 | 2,4-dimethoxy | 2 |
| 1-120 | 2,3-dimethoxy | 2 |
| 1-121 | 3,5-dimethoxy | 2 |
| 1-122 | 3,4-dimethoxy | 2 |

TABLE 2

Derivatives of (1-cyanocyclopropyl)phenylphosphinic esters of the formula (I) b

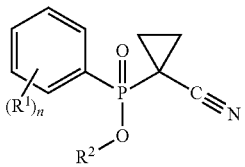

(I) b

| No. | R¹ | n | R² |
|---|---|---|---|
| 2-1 | H | 1 | Me |
| 2-2 | H | 1 | Et |
| 2-3 | 2-F | 1 | Et |
| 2-4 | 3-F | 1 | Et |
| 2-5 | 4-F | 1 | Et |
| 2-6 | 2-Cl | 1 | Et |
| 2-7 | 3-Cl | 1 | Et |
| 2-8 | 4-Cl | 1 | Et |
| 2-9 | 2-Br | 1 | Et |
| 2-10 | 3-Br | 1 | Et |
| 2-11 | 4-Br | 1 | Et |
| 2-12 | 2-I | 1 | Et |
| 2-13 | 3-I | 1 | Et |
| 2-14 | 4-I | 1 | Et |
| 2-15 | 2-Me | 1 | Et |
| 2-16 | 3-Me | 1 | Et |
| 2-17 | 4-Me | 1 | Et |
| 2-18 | 2-OMe | 1 | Et |
| 2-19 | 3-OMe | 1 | Et |
| 2-20 | 4-OMe | 1 | Et |
| 2-21 | 2-$CF_3$ | 1 | Et |
| 2-22 | 3-$CF_3$ | 1 | Et |
| 2-23 | 4-$CF_3$ | 1 | Et |
| 2-24 | 2-Et | 1 | Et |
| 2-25 | 3-Et | 1 | Et |
| 2-26 | 4-Et | 1 | Et |
| 2-27 | 2-OEt | 1 | Et |
| 2-28 | 3-OEt | 1 | Et |
| 2-29 | 4-OEt | 1 | Et |
| 2-30 | 2-CN | 1 | Et |
| 2-31 | 3-CN | 1 | Et |
| 2-32 | 4-CN | 1 | Et |
| 2-33 | 2-COOH | 1 | Et |
| 2-34 | 3-COOH | 1 | Et |
| 2-35 | 4-COOH | 1 | Et |
| 2-36 | 2-COOEt | 1 | Et |
| 2-37 | 3-COOEt | 1 | Et |
| 2-38 | 4-COOEt | 1 | Et |
| 2-39 | 2-SMe | 1 | Et |
| 2-40 | 3-SMe | 1 | Et |
| 2-41 | 4-SMe | 1 | Et |
| 2-42 | 2-SOMe | 1 | Et |
| 2-43 | 3-SOMe | 1 | Et |
| 2-44 | 4-SOMe | 1 | Et |
| 2-45 | 2-$SO_2Me$ | 1 | Et |
| 2-46 | 3-$SO_2Me$ | 1 | Et |
| 2-47 | 4-$SO_2Me$ | 1 | Et |
| 2-48 | 2-SEt | 1 | Et |
| 2-49 | 3-SEt | 1 | Et |
| 2-50 | 4-SEt | 1 | Et |
| 2-51 | 2-$SO_2Et$ | 1 | Et |
| 2-52 | 3-$SO_2Et$ | 1 | Et |
| 2-53 | 4-$SO_2Et$ | 1 | Et |
| 2-54 | 2-$CH_2OMe$ | 1 | Et |
| 2-55 | 3-$CH_2OMe$ | 1 | Et |
| 2-56 | 4-$CH_2OMe$ | 1 | Et |
| 2-57 | 2-$CH_2OEt$ | 1 | Et |
| 2-58 | 3-$CH_2OEt$ | 1 | Et |
| 2-59 | 4-$CH_2OEt$ | 1 | Et |
| 2-60 | 2-$CH_2SMe$ | 1 | Et |
| 2-61 | 3-$CH_2SMe$ | 1 | Et |
| 2-62 | 4-$CH_2SMe$ | 1 | Et |
| 2-63 | 2-$CH_2SEt$ | 1 | Et |
| 2-64 | 3-$CH_2SEt$ | 1 | Et |
| 2-65 | 4-$CH_2SEt$ | 1 | Et |

TABLE 2-continued

Derivatives of (1-cyanocyclopropyl)phenylphosphinic esters of the formula (I) b

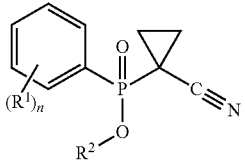

(I) b

| No. | R¹ | n | R² |
|---|---|---|---|
| 2-66 | 2-allyl | 1 | Et |
| 2-67 | 3-allyl | 1 | Et |
| 2-68 | 4-allyl | 1 | Et |
| 2-69 | 2-propargyl | 1 | Et |
| 2-70 | 3-propargyl | 1 | Et |
| 2-71 | 4-propargyl | 1 | Et |
| 2-72 | 2-isopropyl | 1 | Et |
| 2-73 | 3-isopropyl | 1 | Et |
| 2-74 | 4-isopropyl | 1 | Et |
| 2-75 | 2-cyclopropyl | 1 | Et |
| 2-76 | 3-cyclopropyl | 1 | Et |
| 2-77 | 4-cyclopropyl | 1 | Et |
| 2-78 | 2-phenyl | 1 | Et |
| 2-79 | 3-phenyl | 1 | Et |
| 2-80 | 4-phenyl | 1 | Et |
| 2-81 | 2-methoxyethyl | 1 | Et |
| 2-82 | 3-methoxyethyl | 1 | Et |
| 2-83 | 4-methoxyethyl | 1 | Et |
| 2-84 | 2-OH | 1 | Et |
| 2-85 | 3-OH | 1 | Et |
| 2-86 | 4-OH | 1 | Et |
| 2-87 | 2-$NO_2$ | 1 | Et |
| 2-88 | 3-$NO_2$ | 1 | Et |
| 2-89 | 4-$NO_2$ | 1 | Et |
| 2-90 | 2-$NH_2$ | 1 | Et |
| 2-91 | 3-$NH_2$ | 1 | Et |
| 2-92 | 4-$NH_2$ | 1 | Et |
| 2-93 | 2-$Me_2N$ | 1 | Et |
| 2-94 | 3-$Me_2N$ | 1 | Et |
| 2-95 | 4-$Me_2N$ | 1 | Et |
| 2-96 | 2-$CONH_2$ | 1 | Et |
| 2-97 | 3-$CONH_2$ | 1 | Et |
| 2-98 | 4-$CONH_2$ | 1 | Et |
| 2-99 | 2-$CONMe_2$ | 1 | Et |
| 2-100 | 3-$CONMe_2$ | 1 | Et |
| 2-101 | 4-$CONMe_2$ | 1 | Et |
| 2-102 | 2,6-difluoro | 2 | Et |
| 2-103 | 2,5-difluoro | 2 | Et |
| 2-104 | 2,4-difluoro | 2 | Et |
| 2-105 | 2,3-difluoro | 2 | Et |
| 2-106 | 2,6-dichloro | 2 | Et |
| 2-107 | 2,5-dichloro | 2 | Et |
| 2-108 | 2,4-dichloro | 2 | Et |
| 2-109 | 2,3-dichloro | 2 | Et |
| 2-110 | 3,4-dichloro | 2 | Et |
| 2-111 | 3,5-dichloro | 2 | Et |
| 2-112 | 2,6-dimethyl | 2 | Et |
| 2-113 | 2,5-dimethyl | 2 | Et |
| 2-114 | 2,4-dimethyl | 2 | Et |
| 2-115 | 2,3-dimethyl | 2 | Et |
| 2-116 | 3,4-dimethyl | 2 | Et |
| 2-117 | 3,5-dimethyl | 2 | Et |
| 2-118 | 2,6-dimethoxy | 2 | Et |
| 2-119 | 2,5-dimethoxy | 2 | Et |
| 2-120 | 2,4-dimethoxy | 2 | Et |
| 2-121 | 2,3-dimethoxy | 2 | Et |
| 2-122 | 3,5-dimethoxy | 2 | Et |
| 2-123 | 3,4-dimethoxy | 2 | Et |
| 2-124 | ((−)-isomer) H | 1 | Et |
| 2-125 | ((+)-isomer) H | 1 | Et |
| 2-126 | ((−)-isomer) 4-F | 1 | Et |
| 2-127 | ((+)-isomer) 4-F | 1 | Et |
| 2-128 | ((−)-isomer) 4-Cl | 1 | Et |
| 2-129 | ((+)-isomer) 4-Cl | 1 | Et |
| 2-130 | H | 1 | n-propyl |
| 2-131) | H | 1 | isopropyl |
| 2-132 | H | 1 | allyl |
| 2-133 | H | 1 | propargyl |
| 2-134 | H | 1 | n-butyl |
| 2-135 | H | 1 | isobutyl |
| 2-136 | H | 1 | tert-butyl |
| 2-137 | H | 1 | sec-butyl |
| 2-138 | H | 1 | n-pentyl |
| 2-139 | H | 1 | n-hexyl |
| 2-140 | H | 1 | n-octyl |
| 2-141 | H | 1 | cyclopentyl |
| 2-142 | H | 1 | cyclohexyl |
| 2-143 | H | 1 | $ClCH_2CH_2$— |
| 2-144 | H | 1 | $BrCH_2CH_2$— |
| 2-145 | H | 1 | $CF_3CH_2$— |
| 2-146 | H | 1 | $CH_3OCH_2CH_2$— |
| 2-147 | H | 1 | $CH_3SCH_2CH_2$— |
| 2-148 | H | 1 | $C_2H_5CH_2CH_2$— |
| 2-149 | H | 1 | $C_2H_5SCH_2CH_2$— |
| 2-150 | H | 1 | cyclopropyl$CH_2$— |
| 2-151 | H | 1 | $HOCH_2CH_2$— |
| 2-152 | H | 1 | $HOCH_2CH_2CH_2$— |
| 2-153 | H | 1 | $CH_3OCH_2CH_2CH_2$— |
| 2-154 | H | 1 | $HOCH_2=CH—CH_2$— |
| 2-155 | H | 1 | benzyl |
| 2-156 | H | 1 | 2-pyridyl$CH_2$— |
| 2-157 | H | 1 | 2-pyridyl$CH_2CH_2$— |
| 2-158 | 2-F | 1 | n-propyl |
| 2-159 | 2-Cl | 1 | n-propyl |
| 2-160 | 3-Me | 1 | n-propyl |

TABLE 3

Salts of the (1-cyanocyclopropyl)phenylphosphinic acid derivatives where z = 1

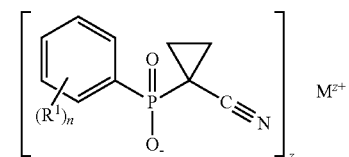

(II)

| No. | R¹ | n | M |
|---|---|---|---|
| 3-1 | H | 1 | isopropylammonium |
| 3-2 | H | 1 | ammonium |
| 3-3 | 2-F | 1 | isopropylammonium |
| 3-4 | 3-F | 1 | isopropylammonium |
| 3-5 | 4-F | 1 | isopropylammonium |
| 3-6 | 2-Cl | 1 | isopropylammonium |
| 3-7 | 3-Cl | 1 | isopropylammonium |
| 3-8 | 4-Cl | 1 | $Na^+$ |
| 3-9 | 2-Br | 1 | ammonium |
| 3-10 | 3-Br | 1 | ammonium |
| 3-11 | 4-Br | 1 | isopropylammonium |
| 3-12 | 2-I | 1 | isopropylammonium |
| 3-13 | 3-I | 1 | isopropylammonium |
| 3-14 | 4-I | 1 | isopropylammonium |
| 3-15 | 2-Me | 1 | isopropylammonium |

TABLE 3-continued

Salts of the (1-cyanocyclopropyl)phenylphosphinic acid derivatives where z = 1

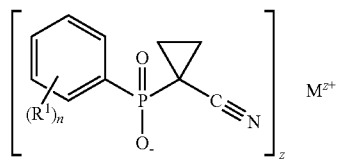
(II)

| No. | R¹ | n | M |
|---|---|---|---|
| 3-16 | 3-Me | 1 | isopropylammonium |
| 3-17 | 4-Me | 1 | isopropylammonium |
| 3-18 | 2-OMe | 1 | isopropylammonium |
| 3-19 | 3-OMe | 1 | isopropylammonium |
| 3-20 | 4-OMe | 1 | isopropylammonium |
| 3-21 | 2-CF$_3$ | 1 | K$^+$ |
| 3-22 | 3-CF$_3$ | 1 | K$^+$ |
| 3-23 | 4-CF$_3$ | 1 | K$^+$ |
| 3-24 | 2-Et | 1 | ammonium |
| 3-25 | 3-Et | 1 | ammonium |
| 3-26 | 4-Et | 1 | ammonium |
| 3-27 | 2-OEt | 1 | isopropylammonium |
| 3-28 | 3-OEt | 1 | isopropylammonium |
| 3-29 | 4-OEt | 1 | isopropylammonium |
| 3-30 | 2-CN | 1 | isopropylammonium |
| 3-31 | 3-CN | 1 | isopropylammonium |
| 3-32 | 4-CN | 1 | isopropylammonium |
| 3-33 | 2-COOMe | 1 | Na$^+$ |
| 3-34 | 3-COOMe | 1 | Na$^+$ |
| 3-35 | 4-COOMe | 1 | Na$^+$ |
| 3-36 | 2-COOEt | 1 | Na$^+$ |
| 3-37 | 3-COOEt | 1 | Na$^+$ |
| 3-38 | 4-COOEt | 1 | Na$^+$ |
| 3-39 | 2-SMe | 1 | Me$_4$N$^+$ |
| 3-40 | 3-SMe | 1 | Me$_4$N$^+$ |
| 3-41 | 4-SMe | 1 | Me$_4$N$^+$ |
| 3-42 | 2-SOMe | 1 | nBu$_4$N$^+$ |
| 3-43 | 3-SOMe | 1 | nBu$_4$N$^+$ |
| 3-44 | 4-SOMe | 1 | nBu$_4$N$^+$ |
| 3-45 | 2-SO$_2$Me | 1 | nBu$_4$N$^+$ |
| 3-46 | 3-SO$_2$Me | 1 | nBu$_4$N$^+$ |
| 3-47 | 4-SO$_2$Me | 1 | nBu$_4$N$^+$ |
| 3-48 | 2-SEt | 1 | ammonium |
| 3-49 | 3-SEt | 1 | ammonium |
| 3-50 | 4-SEt | 1 | ammonium |
| 3-51 | 2-SO$_2$Et | 1 | Li$^+$ |
| 3-52 | 3-SO$_2$Et | 1 | Li$^+$ |
| 3-53 | 4-SO$_2$Et | 1 | Li$^+$ |
| 3-54 | 2-CH$_2$OMe | 1 | Na$^+$ |
| 3-55 | 3-CH$_2$OMe | 1 | Na$^+$ |
| 3-56 | 4-CH$_2$OMe | 1 | Na$^+$ |
| 3-57 | 2-CH$_2$OEt | 1 | (HOCH$_2$CH$_2$)$_3$NH$^+$ |
| 3-58 | 3-CH$_2$OEt | 1 | (HOCH$_2$CH$_2$)$_3$NH$^+$ |
| 3-59 | 4-CH$_2$OEt | 1 | (HOCH$_2$CH$_2$)$_3$NH$^+$ |
| 3-60 | 2-CH$_2$SMe | 1 | HOCH$_2$CH$_2$NH$_3^+$ |
| 3-61 | 3-CH$_2$SMe | 1 | HOCH$_2$CH$_2$NH$_3^+$ |
| 3-62 | 4-CH$_2$SMe | 1 | HOCH$_2$CH$_2$NH$_3^+$ |
| 3-63 | 2-CH$_2$SEt | 1 | HOCH$_2$CH$_2$NH$_3^+$ |
| 3-64 | 3-CH$_2$SEt | 1 | HOCH$_2$CH$_2$NH$_3^+$ |
| 3-65 | 4-CH$_2$SEt | 1 | HOCH$_2$CH$_2$NH$_3^+$ |
| 3-66 | 2-allyl | 1 | ammonium |
| 3-67 | 3-allyl | 1 | ammonium |
| 3-68 | 4-allyl | 1 | ammonium |
| 3-69 | 2-propargyl | 1 | Na$^+$ |
| 3-70 | 3-propargyl | 1 | Na$^+$ |
| 3-71 | 4-propargyl | 1 | Na$^+$ |
| 3-72 | 2-isopropyl | 1 | K$^+$ |
| 3-73 | 3-isopropyl | 1 | K$^+$ |
| 3-74 | 4-isopropyl | 1 | K$^+$ |
| 3-75 | 2-cyclopropyl | 1 | K$^+$ |
| 3-76 | 3-cyclopropyl | 1 | K$^+$ |
| 3-77 | 4-cyclopropyl | 1 | K$^+$ |
| 3-78 | 2-phenyl | 1 | isopropylammonium |
| 3-79 | 3-phenyl | 1 | isopropylammonium |
| 3-80 | 4-phenyl | 1 | isopropylammonium |

TABLE 3-continued

Salts of the (1-cyanocyclopropyl)phenylphosphinic acid derivatives where z = 1

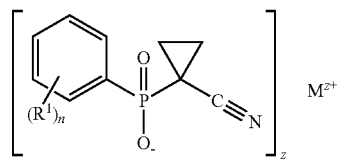
(II)

| No. | R¹ | n | M |
|---|---|---|---|
| 3-81 | 2-methoxyethyl | 1 | isopropylammonium |
| 3-82 | 3-methoxyethyl | 1 | isopropylammonium |
| 3-83 | 4-methoxyethyl | 1 | isopropylammonium |
| 3-84 | 2-OH | 1 | isopropylammonium |
| 3-85 | 3-OH | 1 | isopropylammonium |
| 3-86 | 4-OH | 1 | isopropylammonium |
| 3-87 | 2-NO$_2$ | 1 | Na$^+$ |
| 3-88 | 3-NO$_2$ | 1 | Na$^+$ |
| 3-89 | 4-NO$_2$ | 1 | Na$^+$ |
| 3-90 | 2-NH$_2$ | 1 | Na$^+$ |
| 3-91 | 3-NH$_2$ | 1 | Na$^+$ |
| 3-92 | 4-NH$_2$ | 1 | Na$^+$ |
| 3-93 | 2-Me$_2$N | 1 | K$^+$ |
| 3-94 | 3-Me$_2$N | 1 | K$^+$ |
| 3-95 | 4-Me$_2$N | 1 | K$^+$ |
| 3-96 | 2-CONH$_2$ | 1 | K$^+$ |
| 3-97 | 3-CONH$_2$ | 1 | K$^+$ |
| 3-98 | 4-CONH$_2$ | 1 | K$^+$ |
| 3-99 | 2-CONMe$_2$ | 1 | isopropylammonium |
| 3-100 | 3-CONMe$_2$ | 1 | isopropylammonium |
| 3-101 | 4-CONMe$_2$ | 1 | isopropylammonium |
| 3-102 | 2,6-difluoro | 2 | isopropylammonium |
| 3-103 | 2,5-difluoro | 2 | isopropylammonium |
| 3-104 | 2,4-difluoro | 2 | isopropylammonium |
| 3-105 | 2,3-difluoro | 2 | isopropylammonium |
| 3-106 | 2,6-dichloro | 2 | isopropylammonium |
| 3-107 | 2,5-dichloro | 2 | isopropylammonium |
| 3-108 | 2,4-dichloro | 2 | isopropylammonium |
| 3-109 | 2,3-dichloro | 2 | isopropylammonium |
| 3-110 | 3,4-dichloro | 2 | isopropylammonium |
| 3-111 | 3,5-dichloro | 2 | isopropylammonium |
| 3-112 | 2,6-dimethyl | 2 | isopropylammonium |
| 3-113 | 2,5-dimethyl | 2 | isopropylammonium |
| 3-114 | 2,4-dimethyl | 2 | isopropylammonium |
| 3-115 | 2,3-dimethyl | 2 | isopropylammonium |
| 3-116 | 3,4-dimethyl | 2 | isopropylammonium |
| 3-117 | 3,5-dimethyl | 2 | isopropylammonium |
| 3-118 | 2,6-dimethoxy | 2 | isopropylammonium |
| 3-119 | 2,5-dimethoxy | 2 | isopropylammonium |
| 3-120 | 2,4-dimethoxy | 2 | isopropylammonium |
| 3-121 | 2,3-dimethoxy | 2 | isopropylammonium |
| 3-122 | 3,5-dimethoxy | 2 | isopropylammonium |
| 3-123 | 3,4-dimethoxy | 2 | isopropylammonium |

Spectroscopic data for individual further chemical synthesis examples:

Table example No. 1-1:
$^1$H NMR (400 MHz, CDCl$_3$, δ, ppm) 7.80-7.90 (m, 2H) 7.60-7.68 (m, 1H) 7.45-7.55 (m, 2H) 1.48-1.59 (m, 2H) 1.37-1.48 (m, 2H)

Table example No. 1-2:
$^1$H NMR (400 MHz, CDCl$_3$, δ, ppm) 7.8-7.9 (m, 1H) 7.6-7.7 (m, 1H) 7.3-7.4 (m, 1H) 7.15-7.3 (m, 1H) 1.62-1.75 (m, 2H) 1.45-1.57 (m, 2H)

Table example No. 1-5:
$^1$H NMR (400 MHz, CDCl$_3$, δ, ppm) 7.95-8.10 (m, 1H) 7.45-7.55 (m, 2H) 7.35-7.40 (m, 1H) 1.53-1.60 (m, 2H) 1.70-1.82 (m, 2H)

Table example No. 1-6:
$^1$H NMR (400 MHz, CDCl$_3$, δ, ppm) 7.70-7.80 (m, 2H) 7.55-7.64 (m, 1H) 7.42-7.49 (m, 1H) 1.42-1.59 (m, 4H)

Table example No. 1-17:
$^1$H NMR (400 MHz, CDCl$_3$, δ, ppm) 7.75-7.85 (m, 1H) 7.55-7.62 (m, 1H) 6.95-7.10 (m, 2H) 3.95 (s, 3H) 1.62-1.70 (m, 2H) 1.47-1.54 (m, 2H)

Table example No. 1-19:
$^1$H NMR (400 MHz, CDCl$_3$, δ, ppm) 7.70-7.80 (m, 2H) 6.95-7.05 (m, 2H) 3.85 (s, 3H) 1.49-1.55 (m, 2H) 1.37-1.44 (m, 2H)

Table example No. 1-107:
$^1$H NMR (400 MHz, CDCl$_3$, δ, ppm) 7.85-7.95 (m, 1H) 7.45-7.55 (m, 1H) 7.33-7.40 (m, 1H) 1.69-1.79 (m, 2H) 1.52-1.68 (m, 2H)

Table example No. 2-1:
$^1$H NMR (400 MHz, CDCl$_3$, δ, ppm) 7.86-7.95 (m, 2H) 7.62-7.70 (m, 1H) 7.00-7.10 (m, 2H) 3.87 (d, 3H) 1.88-1.98 (m, 1H) 1.57-1.65 (m, 1H) 1.37-1.48 (m, 2H)

Table example No. 2-2:
$^1$H NMR (400 MHz, CDCl$_3$, δ, ppm) 7.88-7.96 (m, 2H) 7.62-7.68 (m, 1H) 7.50-7.60 (m, 2H) 4.10-4.32 (m, 2H) 1.87-1.96 (m, 1H) 1.53-1.63 (m, 2H) 1.45-1.50 (m, 1H) 1.42 (t, 3H)

Table example No. 2-3:
$^1$H NMR (400 MHz, CDCl$_3$, δ, ppm) 7.80-7.92 (m, 1H) 7.60-7.70 (m, 1H) 7.29-7.34 (m, 1H) 7.19-7.28 (m, 1H) 4.18-4.35 (m, 2H) 1.88-2.00 (m, 1H) 1.47-1.65 (m, 3H) 1.95 (t, 3H)

Table example No. 2-6:
$^1$H NMR (400 MHz, CDCl$_3$, δ, ppm) 7.95-8.06 (m, 1H) 7.50-7.60 (m, 2H) 7.33-7.50 (m, 1H) 4.18-4.37 (m, 2H) 1.85-2.15 (m, 1H) 1.55-1.73 (m, 3H) 1.47 (t, 3H)

Table example No. 2-7:
$^1$H NMR (400 MHz, CDCl$_3$, δ, ppm) 7.76-7.91 (m, 2H) 7.6-7.65 (m, 1H) 7.48-7.55 (m, 1H) 4.15-4.35 (m, 2H) 1.87-1.97 (m, 1H) 1.39-1.48 (m, 1H) 1.39-1.50 (m, 2H) 1.42 (t, 3H)

Table example No. 2-8:
$^1$H NMR (400 MHz, CDCl$_3$, δ, ppm) 7.80-7.90 (m, 2H) 7.49-7.56 (m, 2H) 4.10-4.30 (m, 2H) 1.87-1.96 (m, 1H) 1.58-1.65 (m, 1H) 1.35-1.48 (m, 2H) 1.42 (t, 3H)

Table example No. 2-16:
$^1$H NMR (400 MHz, CDCl$_3$, δ, ppm) 7.68-7.76 (m, 2H) 7.40-7.48 (m, 2H) 4.09-4.30 (m, 2H) 2.43 (s, 3H) 1.86-1.95 (m, 1H) 1.52-1.63 (m, 1H) 1.32-1.47 (m, 2H) 1.41 (t, 3H)

Table example No. 2-17:
$^1$H NMR (400 MHz, CDCl$_3$, δ, ppm) 7.78-7.84 (m, 2H) 7.32-7.38 (m, 2H) 4.10-4.30 (m, 2H) 2.44 (s, 3H) 1.85-1.96 (m, 1H) 1.52-1.62 (m, 1H) 1.35-1.46 (m, 2H) 1.39 (t, 3H)

Table example No. 2-18:
$^1$H NMR (400 MHz, CDCl$_3$, δ, ppm) 7.78-7.85 (m, 1H) 7.55-7.63 (m, 1H) 7.05-7.10 (m, 1H) 6.97-7.08 (m, 1H) 3.95 (s, 3H) 1.62-1.70 (m, 2H) 1.47-1.53 (m, 2H)

Table example No. 2-19:
$^1$H NMR (400 MHz, CDCl$_3$, δ, ppm) 7.39-7.52 (m, 3H) 7.13-7.20 (m, 1H) 4.08-4.22 (m, 2H) 3.78 (s, 3H) 1.85-1.93 (m, 1H) 1.53-1.62 (m, 1H) 1.37-1.48 (m, 2H) 1.42 (t, 3H)

Table example No. 2-20:
$^1$H NMR (400 MHz, CDCl$_3$, δ, ppm) 7.80-7.89 (m, 2H) 7.00-7.08 (m, 2H) 4.08-4.27 (m, 2H) 3.88 (s, 3H) 1.82-1.92 (m, 1H) 1.52-1.60 (m, 1H) 1.37-1.48 (m, 2H) 1.42 (t, 3H)

Table example No. 2-34:
$^1$H NMR (400 MHz, CDCl$_3$, δ, ppm) 8.62-8.70 (m, 1H) 8.34-8.38 (m, 2H) 8.12-8.20 (m, 1H) 7.67-7.92 (m, 1H) 4.18-4.35 (m, 2H) 1.92-2.00 (m, 1H) 1.59-1.69 (m, 1H) 1.40-1.55 (m, 2H)

Table example No. 2-37:
$^1$H NMR (400 MHz, CDCl$_3$, δ, ppm) 8.51-8.58 (m, 1H) 8.30-8.35 (m, 1H) 8.08-8.14 (m, 1H) 7.62-7.68 (m, 1H) 4.43 (t, 2H) 4.15-4.32 (m, 2H) 1.89-2.00 (m, 1H) 1.59-1.68 (m, 1H) 1.40-1.52 (m, 2H) 1.48 (t, 3H) 1.40 (t, 3H)

Table example No. 2-61:
$^1$H NMR (400 MHz, CDCl$_3$, δ, ppm) 7.78-7.85 (m, 2H) 7.62-7.66 (m, 1H) 7.48-7.56 (m, 2H) 4.14-4.32 (m, 2H) 3.18-3.30 (m, 2H) 2.02 (s, 3H) 1.88-1.98 (m, 1H) 1.58-1.68 (m, 1H) 1.38-1.50 (m, 2H) 1.43 (t, 3H)

Table example No. 2-106:
$^1$H NMR (400 MHz, CDCl$_3$, δ, ppm) 7.36-7.50 (m, 3H) 4.19-4.40 (m, 2H) 1.92-2.02 (m, 1H) 1.80-1.90 (m, 1H) 1.60-1.73 (m, 2H) 1.45 (t, 3H)

Table example No. 2-108:
$^1$H NMR (400 MHz, CDCl$_3$, δ, ppm) 7.90-8.00 (m, 1H) 7.54-7.58 (m, 1H) 7.39-7.44 (m, 1H) 4.18-4.36 (m, 2H) 1.88-1.98 (m, 1H) 1.56-1.72 (m, 3H) 1.44 (t, 3H)

Table example No. 2-111:
$^1$H NMR (400 MHz, CDCl$_3$, δ, ppm) 7.75-7.80 (dd, 2H) 7.62 (d, 1H) 4.15-4.35 (m, 2H) 1.88-1.98 (m, 1H) 1.60-1.69 (m, 1H) 1.42-1.50 (m, 2H) 1.44 (t, 3H)

Table example No. 2-124:
$^1$H NMR (400 MHz, CDCl$_3$, δ, ppm) 7.87-7.96 (m, 2H) 7.62-7.68 (m, 1H) 7.50-7.60 (m, 2H) 4.10-4.32 (m, 2H) 1.87-1.96 (m, 1H) 1.53-1.63 (m, 1H) 1.42 (t, 3H) 1.45-1.50 (m, 2H) $[α]^{23}_{589}$ −9.69°

Table example No. 2-125:
$^1$H NMR (400 MHz, CDCl$_3$, δ, ppm) 7.87-7.96 (m, 2H) 7.62-7.68 (m, 1H) 7.50-7.60 (m, 2H) 4.10-4.32 (m, 2H) 1.87-1.96 (m, 1H) 1.53-1.63 (m, 1H) 1.42 (t, 3H) 1.45-1.50 (m, 2H)

Table example No. 2-130:
$^1$H NMR (400 MHz, CDCl$_3$, δ, ppm) 7.86-7.96 (m, 2H) 7.60-7.68 (m, 1H) 7.50-7.58 (m, 2H) 4.00-4.20 (m, 2H) 1.86-1.96 (m, 1H) 1.77-1.86 (m, 2H) 1.56-1.63 (m, 1H) 1.35-1.48 (m, 2H) 1.03 (t, 3H)

Table example No. 2-131:
$^1$H NMR (400 MHz, CDCl$_3$, δ, ppm) 7.88-7.96 (m, 2H) 7.60-7.66 (m, 1H) 7.50-7.58 (m, 2H) 4.69-4.81 (m, 1H) 1.84-1.95 (m, 1H) 1.52-1.62 (m, 1H) 1.50 (d, 3H) 1.30-1.48 (m, 2H) 1.39 (d, 3H)

Table example No. 2-132:
$^1$H NMR (400 MHz, CDCl$_3$, δ, ppm) 7.86-7.96 (m, 2H) 7.62-7.70 (m, 1H) 7.50-7.60 (m, 2H) 5.97-6.08 (m, 1H) 5.40-5.50 (m, 1H) 5.30-5.38 (m, 1H) 4.52-4.73 (m, 2H) 1.85-2.00 (m, 1H) 1.56-1.67 (m, 1H) 1-37-1.50 (m, 2H)

Table example No. 2-134:
$^1$H NMR (400 MHz, CDCl$_3$, δ, ppm) 7.87-7.96 (m, 2H) 7.62-7.68 (m, 1H) 7.51-7.60 (m, 2H) 4.03-4.24 (m, 2H) 1.86-1.96 (m, 1H) 1.73-1.82 (m, 2H) 1.56-1.65 (m, 1H) 1.35-1.55 (m, 4H) 0.96 (t, 3H)

Table example No. 2-135:
$^1$H NMR (400 MHz, CDCl$_3$, δ, ppm) 7.86-7.95 (m, 2H) 7.62-7.68 (m, 1H) 7.51-7.60 (m, 2H) 3.72-4.00 (m, 2H) 2.03-2.14 (m, 1H) 1.86-1.98 (m, 1H) 1.57-1.65 (m, 1H) 1.38-1.50 (m, 2H) 1.02 (d, 6H)

Table example No. 2-141:
$^1$H NMR (400 MHz, CDCl$_3$, δ, ppm) 7.85-7.93 (m, 2H) 7.62-7.68 (m, 1H) 7.52-7.68 (m, 2H) 4.95-5.03 (m, 1H) 1.35-2.13 (m, 12H)

Table example No. 2-142:
$^1$H NMR (400 MHz, CDCl$_3$, δ, ppm) 7.87-7.98 (m, 2H) 7.62-7.68 (m, 1H) 7.50-7.60 (m, 2H) 4.45-4.53 (m, 1H) 1.25-2.10 (m, 14H)

Table example No. 2-154:
$^1$H NMR (400 MHz, CDCl$_3$, δ, ppm) 7.84-7.95 (m, 2H) 7.50-7.70 (m, 3H) 5.76-5.95 (m, 2H) 4.70-4.95 (m, 2H) 4.15-4.25 (m, 2H) 1.86-1.96 (m, 1H) 1.55-1.67 (m, 1H) 1.40-1.50 (m, 2H)

Table example No. 2-155:
$^1$H NMR (400 MHz, CDOD, δ, ppm) 7.86-7.96 (m, 2H) 7.70-7.77 (m, 2H) 7.58-7.67 (m, 2H) 7.35-7.55 (m, 5H) 5.25-5.30 (m, 2H) 1.45-1.86 (m, 4H)

Table example No. 2-156:
$^1$H NMR (400 MHz, CDCl$_3$, δ, ppm) 8.69-8.72 (d, 1H) 7.90-8.02 (m, 3H) 7.43-7.80 (m, 5H) 5.35-5.48 (m, 2H) 1.90-2.05 (m, 1H) 1.60-1.69 (m, 1H) 1.40-1.60 (m, 2H)

Table example No. 2-157:
$^1$H NMR (400 MHz, CDCl$_3$, δ, ppm) 8.88-8.92 (m, 1H) 8.33-8.40 (m, 1H) 7.50-7.76 (m, 7H) 4.45-4.67 (m, 2H) 3.53-3.65 (m, 2H) 1.80-1.90 (m, 1H) 1.56-1.65 (m, 1H) 1.30-1.48 (m, 2H)

Table example No. 3-1:
$^1$H NMR (400 MHz, CDCl$_3$, δ, ppm) 7.79-7.86 (m, 2H) 7.52-7.60 (m, 1H) 7.42-7.50 (m, 2H) 3.28-3.40 (m, 1H) 1.40-1.50 (m, 2H) 1.25-1.35 (m, 2H) 1.26 (d, 6H).

Table example No. 3-2:
$^1$H NMR (400 MHz, D$_2$O, δ, ppm) 7.65-7.80 (m, 2H) 7.40-7.55 (m, 3H) 1.29-1.39 (m, 4H).

Table example No. 3-3:
$^1$H NMR (400 MHz, CD$_3$OD, δ, ppm) 7.85-7.96 (m, 1H) 7.48-7.56 (m, 1H) 7.22-7.30 (m, 1H) 7.12-7.20 (m, 1H) 3.38-3.48 (m, 1H) 1.52-1.63 (m, 2H) 1.30-1.38 (m, 2H) 1.30 (d, 6H).

Table example No. 3-6:
$^1$H NMR (400 MHz, D$_2$O, δ, ppm) 7.85-7.93 (m, 1H) 7.43-7.52 (m, 2H) 7.47-7.50 (m, 1H) 3.37-3.48 (m, 1H) 1.45-1.56 (m, 4H) 1.22 (d, 6H).

Table example No. 3-7:
$^1$H NMR (400 MHz, CDCl$_3$, δ, ppm) 7.67-7.80 (m, 2H) 7.42-7.48 (m, 1H) 7.35-7.40 (m, 1H) 3.12-3.25 (m, 1H) 1.18-1.35 (m, 4H) 1.25 (d, 6H).

Table example No. 3-18:
$^1$H NMR (400 MHz, CDCl$_3$, δ, ppm) 7.70-7.80 (m, 1H) 7.38-7.45 (m, 1H) 6.86-7.00 (m, 2H) 3.89 (s, 3H) 3.03-3.15 (m, 1H) 1.18-1.38 (m, 4H) 1.20 (d, 6H).

Table example No. 3-106:
$^1$H NMR (400 MHz, D$_2$O, δ, ppm) 7.40-7.48 (m, 2H) 7.33 (t, 1H) 3.37-3.45 (m, 1H) 1.52-1.60 (m, 4H) 1.21 (d, 6H).

The (1-alkoxycarbonylcyclopropyl)phenylphosphinic acid derivatives of the formula (4) described in scheme 4 and (1-aminocarbonylcyclopropyl)phenylphosphinic acid derivatives of the formula (5) are novel and therefore likewise form part of the subject matter of the present application. Typical representatives of these reactants are listed in tables 4 and 5.

PREPARATION EXAMPLES

Methyl 1-[ethoxy(phenyl)phosphoryl]cyclopropanecarboxylate

Table Example No. 4-2 a) Methyl[ethoxy(phenyl)phosphoryl]acetate 3.859 g (25.227 mmol) of methyl bromoacetate were added gradually at room temperature to 5.5 g (25.227 mmol) of phenyl diethylphosphite, then the mixture was heated to 90° C. for 3 h and the bromoethane which formed was distilled off. After cooling, the mixture was taken up in dichloromethane, washed with NaCl solution and, after drying with Na$_2$SO$_4$, concentrated by rotary evaporation. This gave 6.130 g (90.29% of theory) of methyl[ethoxy(phenyl)phosphoryl]acetate.
$^1$H NMR (400 MHz, CDCl$_3$, δ, ppm) 7.78-7.85 (m, 2H) 7.55-7.60 (m, 1H) 7.46-7.55 (m, 2H) 3.98-4.23 (m, 2H) 3.62 (s, 3H) 3.1-3.18 (d, 2H) 1.35 (t, 3H)

b) Methyl 1-[ethoxy(phenyl)phosphoryl]cyclopropanecarboxylate 1.2 g (4.954 mmol) of methyl[ethoxy(phenyl)phosphoryl]acetate were dissolved in 50 ml of DMSO, 2.054 g of K2CO3 (14.863 mmol) were added and, after addition of 2.792 g (14.863 mmol) of 1,2-dibromoethane, the mixture was stirred at room temperature for 18 h. After concentrating by rotary evaporation, the mixture was taken up in dichloromethane, washed with water and, after drying with Na$_2$SO$_4$, concentrated by rotary evaporation.

This gave 1.328 g (100% of theory) of methyl[ethoxy(phenyl)phosphoryl]cyclopropanecarboxylate.
$^1$H NMR (400 MHz, CDCl$_3$, δ, ppm) 7.85-7.93 (m, 2H) 7.50-7.58 (m, 1H) 7.43-7.50 (m, 2H) 4.00-4.20 (m, 2H) 3.59 (s, 3H) 1.52-1.80 (m, 4H) 1.33 (t, 3H).

TABLE 4

Derivatives of (1-alkoxycarbonylcyclopropyl)phenylphosphinic esters of the formula (4), where n = 1

(4)

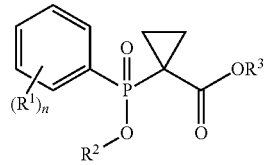

| No. | R$^1$ | R$^2$ | R$^3$ |
|---|---|---|---|
| 4-1 | H | Me | Me |
| 4-2 | H | Et | Me |
| 4-3 | H | Me | Et |
| 4-4 | H | Et | Et |
| 4-5 | H | n-propyl | Me |
| 4-6 | H | n-propyl | Et |
| 4-7 | H | n-propyl | n-butyl |
| 4-8 | 2-F | Me | Me |
| 4-9 | 4-F | Me | Me |
| 4-10 | 4-Cl | Et | Me |
| 4-11 | 4-Me | Et | Me |
| 4-12 | 3-Me | Et | Me |
| 4-13 | 3-Br | Et | Me |
| 4-14 | 3-CF$_3$ | Et | Me |

TABLE 5

Derivatives of (1-aminocarbonylcyclopropyl)phenylphosphinic esters (5), where n = 1

(5)

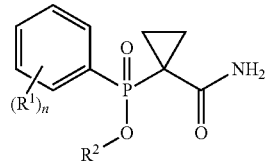

| No. | R$^1$ | R$^2$ |
|---|---|---|
| 5-1 | H | Me |
| 5-2 | H | Et |
| 5-3 | H | n-propyl |
| 5-4 | H | n-butyl |
| 5-5 | 2-F | Me |
| 5-6 | 2-F | Et |
| 5-7 | 4-F | Me |
| 5-8 | 4-F | Et |

TABLE 5-continued

Derivatives of (1-aminocarbonylcyclo-
propyl)phenylphosphinic
esters (5), where n = 1

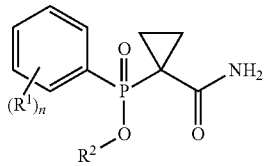

(5)

| No. | R¹ | R² |
|---|---|---|
| 5-9 | 4-Cl | Et |
| 5-10 | 3-Me | Me |
| 5-11 | 3-Me | Et |
| 5-12 | 3-CF₃ | Me |

Spectroscopic data of chemical example No. 5-2:

Ethyl(1-carbamoylcyclopropyl)phenylphosphinate $^1$H NMR (400 MHz, CDCl$_3$, δ, ppm) 8.00-8.05 (s, 1H) 7.77-7.84 (m, 2H) 7.55-7.63 (m, 1H) 7.45-7.53 (m, 2H) 5.60-5.70 (s, 1H) 3.95-4.20 (m, 2H) 1.10-1.63 (m, 4H) 1.35 (t, 3H).

The present invention provides for the use of at least one compound selected from the group consisting of derivatives of (1-cyanocyclopropyl)phenylphosphinic acids and esters thereof, of the formula (I), and salts thereof, of the formula (II), and of any desired mixtures of the derivatives of (1-cyanocyclopropyl)phenylphosphinic acids, esters thereof, of the formula (I), and/or salts thereof, of the formula (II), with active agrochemical ingredients as defined below, for enhancing the resistance of plants to abiotic stress factors, preferably to drought stress (i.e. stress situations triggered by the stress factors of aridity and/or lack of water), especially for enhancing plant growth and/or for increasing plant yield.

The present invention further provides a spray solution for treatment of plants, comprising an amount, effective for enhancing the resistance of plants to abiotic stress factors, preferably to drought stress, of at least one compound selected from the group consisting of derivatives of (1-cyanocyclopropyl)phenylphosphinic acids and esters thereof, of the formula (I), and salts thereof, of the formula (II). Abiotic stress conditions which can be relativized may include, for example, drought, cold and hot conditions, osmotic stress, waterlogging, elevated soil salinity, elevated exposure to minerals, ozone conditions, strong light conditions, limited availability of nitrogen nutrients, limited availability of phosphorus nutrients.

In one embodiment, it is possible, for example, that the derivatives, provided in accordance with the invention, of (1-cyanocyclopropyl)phenylphosphinic acids or esters thereof, of the formula (I), and/or salts thereof, of the formula (II), are applied by spray application to appropriate plants or plant parts to be treated. The derivatives of (1-cyanocyclopropyl)phenylphosphinic acids or esters thereof, of the formula (I), and/or salts thereof, of the formula (II), are used in accordance with the invention preferably with a dosage between 0.0005 and 3 kg/ha, more preferably between 0.001 and 2 kg/ha, especially preferably between 0.005 and 1 kg/ha. When, in the context of the present invention, abscisic acid is used simultaneously with one or more derivatives of (1-cyanocyclopropyl)phenylphosphinic acid or esters thereof, of the formula (I), and/or salts thereof, of the formula (II), for example in the context of a joint preparation or formulation, abscisic acid is preferably added in a dosage between 0.001 and 3 kg/ha, more preferably between 0.005 and 2 kg/ha, especially preferably between 0.01 and 1 kg/ha.

The term "resistance to abiotic stress" is understood in the context of the present invention to mean various kinds of advantages for plants. Such advantageous properties are manifested, for example, in the following improved plant characteristics: improved root growth with regard to surface area and depth, increased stolon and tiller formation, stronger and more productive stolons and tillers, improvement in shoot growth, increased lodging resistance, increased shoot base diameter, increased leaf area, higher yields of nutrients and constituents, for example carbohydrates, fats, oils, proteins, vitamins, minerals, essential oils, dyes, fibers, better fiber quality, earlier flowering, increased number of flowers, reduced content of toxic products such as mycotoxins, reduced content of residues or disadvantageous constituents of any kind, or better digestibility, improved storage stability of the harvested material, improved tolerance to disadvantageous temperatures, improved tolerance to drought, aridity and lack of water (though aridity and lack of water similarly trigger drought stress), and also oxygen deficiency as a result of waterlogging, improved tolerance to elevated salt contents in soil and water, enhanced tolerance to ozone stress, improved compatibility with respect to herbicides and other crop treatment compositions, improved water absorption and photosynthesis performance, advantageous plant properties, for example acceleration of ripening, more homogeneous ripening, greater attractiveness to beneficial animals, improved pollination, or other advantages well known to a person skilled in the art.

More particularly, the inventive use exhibits the advantages described in spray application to plants and plant parts. Combinations of one or more derivatives of (1-cyanocyclopropyl)phenylphosphinic acid or esters thereof, of the formula (I), and/or salts thereof, of the formula (II), with substances including insecticides, attractants, acaricides, fungicides, nematicides, herbicides, growth regulators, safeners, substances which influence plant maturity, and bactericides can likewise be employed in the control of plant disorders in the context of the present invention. The combined use of one or more derivatives of (1-cyanocyclopropyl)phenylphosphinic acid or esters thereof, of the formula (I), and/or salts thereof, of the formula (II), with genetically modified varieties in relation to elevated abiotic stress tolerance is additionally likewise possible.

As is known, some of the various kinds of advantages for plants, which have been mentioned above, can be combined, and generally applicable terms can be used to describe them. Such terms are, for example, the following names: phytotonic effect, resistance to stress factors, less plant stress, plant health, healthy plants, plant fitness, plant wellness, plant concept, vigor effect, stress shield, protective shield, crop health, crop health properties, crop health products, crop health management, crop health therapy, plant health properties, plant health products, plant health management, plant health therapy, greening effect or regreening effect, freshness, or other terms with which a person skilled in the art is quite familiar.

In the context of the present invention, a good effect on resistance to abiotic stress is understood to mean, without limitation, at least an emergence improved by generally 3%, especially more than 5%, preferably more than 10%, at least a yield enhanced by generally 3%, especially more than 5%, preferably more than 10%, at least a root development improved by generally 3%, especially more than 5%, preferably more than 10%, at least a shoot size rising by generally 3%, especially more than 5%, preferably more than 10%, at least a leaf area increased by generally 3%, especially more than 5%, preferably more than 10%, at least a photosynthesis performance improved by generally 3%, especially more than 5%, preferably more than 10%, and/or at least a flower formation improved by generally 3%, especially more than 5%, preferably more than 10%, and the effects may occur individually or else in any combination of two or more effects.

The present invention further provides a spray solution for treatment of plants, comprising an amount, effective for enhancing the resistance of plants to abiotic stress factors, preferably to stress factors which cause drought stress, of at least one derivative of (1-cyanocyclopropyl)phenylphosphinic acid or esters thereof, of the formula (I), and/or salts thereof, of the formula (II). The spray solution may comprise other customary constituents, such as solvents, formulation aids, especially water. Further constituents may include active agrochemical ingredients described below.

The present invention further provides for the use of corresponding spray solutions for enhancing the resistance of plants to abiotic stress factors, preferably to drought stress. The remarks which follow apply both to the inventive use of the derivatives of (1-cyanocyclopropyl)phenylphosphinic acid or esters thereof, of the formula (I), and/or salts thereof, of the formula (II), per se and to the corresponding spray solutions.

In accordance with the invention, it has additionally been found that the application, to plants or in their environment, of derivatives of (1-cyanocyclopropyl)phenylphosphinic acid or esters thereof, of the formula (I), and/or salts thereof, of the formula (II), in combination with at least one fertilizer as defined below is possible.

Fertilizers which can be used in accordance with the invention together with the derivatives of (1-cyanocyclopropyl) phenylphosphinic acid or esters thereof, of the formula (I), and/or salts thereof, of the formula (II), elucidated in detail above are generally organic and inorganic nitrogen-containing compounds, for example ureas, urea/formaldehyde condensation products, amino acids, ammonium salts and ammonium nitrates, potassium salts (preferably chlorides, sulfates, nitrates), salts of phosphoric acid and/or salts of phosphorous acid (preferably potassium salts and ammonium salts). In this context, particular mention should be made of the NPK fertilizers, i.e. fertilizers which contain nitrogen, phosphorus and potassium, calcium ammonium nitrate, i.e. fertilizers which additionally contain calcium, or ammonia nitrate sulfate (formula $(NH_4)_2SO_4\ NH_4NO_3$), ammonium phosphate and ammonium sulfate. These fertilizers are common knowledge to those skilled in the art; see also, for example, Ullmann's Encyclopedia of Industrial Chemistry, 5th edition, Vol. A 10, pages 323 to 431, Verlagsgesellschaft, Weinheim, 1987.

The fertilizers may also contain salts of micronutrients (preferably calcium, sulfur, boron, manganese, magnesium, iron, boron, copper, zinc, molybdenum and cobalt) and phytohormones (for example vitamin B1 and indole-3-acetic acid) or mixtures thereof. Fertilizers used in accordance with the invention may also contain other salts such as monoammonium phosphate (MAP), diammonium phosphate (DAP), potassium sulfate, potassium chloride, magnesium sulfate. Suitable amounts for the secondary nutrients, or trace elements, are amounts of 0.5 to 5% by weight, based on the overall fertilizer. Further possible ingredients are crop protection compositions, insecticides or fungicides, growth regulators or mixtures thereof. This will be explained in more detail below.

The fertilizers can be used, for example, in the form of powders, granules, prills or compactates. However, the fertilizers can also be used in liquid form, dissolved in an aqueous medium. In this case, dilute aqueous ammonia can also be used as a nitrogen fertilizer. Further possible ingredients for fertilizers are described, for example, in Ullmann's Encyclopedia of Industrial Chemistry, 5th edition, volume A 10, pages 363 to 401, DE-A 41 28 828, DE-A 19 05 834 and DE-A 196 31 764. The general composition of the fertilizers which, within the context of the present invention, may take the form of straight and/or compound fertilizers, for example composed of nitrogen, potassium or phosphorus, may vary within a wide range. In general, a content of 1 to 30% by weight of nitrogen (preferably 5 to 20% by weight), 1 to 20% by weight of potassium (preferably 3 to 15% by weight) and a content of 1 to 20% by weight of phosphorus (preferably 3 to 10% by weight) is advantageous. The microelement content is usually in the ppm range, preferably in the range from 1 to 1000 ppm.

In the context of the present invention, the fertilizer and one or more derivatives of (1-cyanocyclopropyl)phenylphosphinic acid or esters thereof, of the formula (I), and/or one or more salts, of the formula (II), may be administered simultaneously, i.e. synchronously. However, it is also possible first to apply the fertilizer and then one or more derivatives of (1-cyanocyclopropyl)phenylphosphinic acid or esters thereof, of the formula (I), or first to apply one or more salts of the formula (II) and then the fertilizer. In the case of nonsynchronous application of one or more derivatives of (1-cyanocyclopropyl)phenylphosphinic acid or esters thereof, of the formula (I), and/or of one or more salts, of the formula (II), and the fertilizer, the application in the context of the present invention is, however, effected in a functional relationship, especially within a period of generally 24 hours, preferably 18 hours, more preferably 12 hours, specifically 6 hours, more specifically 4 hours, even more specifically within 2 hours. In very particular embodiments of the present invention, the inventive compound of the formula (I) and the fertilizer are applied within a time frame of less than 1 hour, preferably less than 30 minutes, more preferably less than 15 minutes.

The derivatives of (1-cyanocyclopropyl)phenylphosphinic acid or esters thereof, of the formula (I), and/or salts thereof, of the formula (II), to be used in accordance with the invention, can preferably be applied to the following plants, if appropriate in combination with fertilizers, though the enumeration which follows is not limiting.

Preferred plants are those from the group of the useful plants, ornamental plants, turfgrass types, commonly used trees which are employed as ornamentals in public and domestic areas, and forestry trees. Forestry trees include trees for the production of timber, cellulose, paper and products made from parts of the trees. The term "useful plants" as used here refers to crop plants which are employed as plants for obtaining foods, animal feeds, fuels or for industrial purposes.

The useful plants include, for example, the following types of plants: triticale, durum (hard wheat), turf, vines, cereals, for example wheat, barley, rye, oats, hops, rice, corn and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries;

legumes, for example beans, lentils, peas and soybeans; oil crops, for example oilseed rape, mustard, poppies, olives, sunflowers, coconuts, castor oil plants, cacao beans and peanuts; cucurbits, for example pumpkin/squash, cucumbers and melons; fiber plants, for example cotton, flax, hemp and jute; citrus fruit, for example oranges, lemons, grapefruit and tangerines; vegetables, for example spinach, lettuce, asparagus, cabbage species, carrots, onions, tomatoes, potatoes and bell peppers; Lauraceae, for example avocado, Cinnamomum, camphor, or also plants such as tobacco, nuts, coffee, eggplant, sugarcane, tea, pepper, grapevines, hops, bananas, latex plants and ornamentals, for example flowers, shrubs, deciduous trees and coniferous trees. This enumeration is not a limitation.

The following plants are considered to be particularly suitable target crops for the application of the method according to the invention: oats, rye, triticale, durum, cotton, eggplant, turf, pome fruit, stone fruit, soft fruit, corn, wheat, barley, cucumber, tobacco, vines, rice, cereals, pear, peppers, beans, soybeans, oilseed rape, tomato, bell pepper, melons, cabbage, potatoes and apples.

Examples of trees which can be improved in accordance with the method according to the invention include: *Abies* sp., *Eucalyptus* sp., *Picea* sp., *Pinus* sp., *Aesculus* sp., *Platanus* sp., *Tilia* sp., *Acer* sp., *Tsuga* sp., *Fraxinus* sp., *Sorbus* sp., *Betula* sp., *Crataegus* sp., *Ulmus* sp., *Quercus* sp., *Fagus* sp., *Salix* sp., *Populus* sp.

Preferred trees which can be improved by the method according to the invention include: from the tree species *Aesculus*: *A. hippocastanum, A. pariflora, A. carnea*; from the tree species *Platanus*: *P. aceriflora, P. occidentalis, P. racemosa*; from the tree species *Picea*: *P. abies*; from the tree species *Pinus*: *P. radiate, P. ponderosa, P. contorta, P. sylvestre, P. elliottii, P. montecola, P. albicaulis, P. resinosa, P. palustris, P. taeda, P. flexilis, P. jeffregi, P. baksiana, P. strobes*; from the tree species *Eucalyptus*: *E. grandis, E. globulus, E. camadentis, E. nitens, E. obliqua, E. regnans, E. pilularus*.

Particularly preferred trees which can be improved by the method according to the invention include: from the tree species *Pinus*: *P. radiate, P. ponderosa, P. contorta, P. sylvestre, P. strobes*; from the tree species *Eucalyptus*: *E. grandis, E. globulus* and *E. camadentis*.

Particularly preferred trees which can be improved by the method according to the invention include: horse chestnut, Platanaceae, linden tree, maple tree.

The present invention can also be applied to any turfgrass types, including cool-season turfgrasses and warm-season turfgrasses. Examples of cool-season turfgrasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poa annua* L.), upland bluegrass (*Poa glaucantha* Gaudin), wood bluegrass (*Poa nemoralis* L.) and bulbous bluegrass (*Poa bulbosa* L.); bentgrasses (*Agrostis* spp.) such as creeping bentgrass (*Agrostis palustris* Huds.), colonial bentgrass (*Agrostis tenuis* Sibth.), velvet bentgrass (*Agrostis canina* L.), South German Mixed Bentgrass (*Agrostis* spp. including *Agrostis tenius* Sibth., *Agrostis canina* L., and *Agrostis palustris* Huds.), and redtop (*Agrostis alba* L.); fescues (*Festuca* spp.), such as red fescue (*Festuca rubra* L. spp. *rubra*), creeping fescue (*Festuca rubra* L.), chewings fescue (*Festuca rubra commutata* Gaud.), sheep fescue (*Festuca ovina* L.), hard fescue (*Festuca longifolia* Thuill.), hair fescue (*Festucu capillata* Lam.), tall fescue (*Festuca arundinacea* Schreb.) and meadow fescue (*Festuca elanor* L.);

ryegrasses (*Lolium* spp.), such as annual ryegrass (*Lolium multiflorum* Lam.), perennial ryegrass (*Lolium perenne* L.) and italian ryegrass (*Lolium multiflorum* Lam.);

and wheatgrasses (*Agropyron* spp.), such as fairway wheatgrass (*Agropyron cristatum* (L.) Gaertn.), crested wheatgrass (*Agropyron desertorum* (Fisch.) Schult.) and western wheatgrass (*Agropyron smithii* Rydb.).

Examples of further cool-season turfgrasses are beachgrass (*Ammophila breviligulata* Fern.), smooth bromegrass (*Bromus inermis* Leyss.), cattails such as Timothy (*Phleum pratense* L.), sand cattail (*Phleum subulatum* L.), orchard grass (*Dactylis glomerata* L.), weeping alkaligrass (*Puccinellia distans* (L.) Parl.) and crested dog's-tail (*Cynosurus cristatus* L.).

Examples of warm-season turfgrasses are Bermuda grass (*Cynodon* spp. L. C. Rich), zoysia grass (*Zoysia* spp. Willd.), St. Augustine grass (*Stenotaphrum secundatum* Walt Kuntze), centipede grass (*Eremochloa ophiuroides* Munro Hack.), carpet grass (*Axonopus affinis* Chase), Bahia grass (*Paspalum notatum* Flugge), Kikuyu grass (*Pennisetum clandestinum* Hochst. ex Chiov.), buffalo grass (*Buchloe dactyloids* (Nutt.) Engelm.), Blue gramma (*Bouteloua gracilis* (H.B.K.) Lag. ex Griffiths), seashore paspalum (*Paspalum vaginatum* Swartz) and sideoats grama (*Bouteloua curtipendula* (Michx.) Torr.). Cool-season turfgrasses are generally preferred for the use in accordance with the invention. Particular preference is given to bluegrass, bentgrass and redtop, fescues and ryegrasses. Bentgrass is especially preferred.

More preferably, plants of the plant cultivars which are commercially available or are in use are treated in accordance with the invention. Plant cultivars are understood to mean plants which have new properties ("traits") and which have been obtained by conventional breeding, by mutagenesis or with the aid of recombinant DNA techniques. Crop plants may accordingly be plants which can be obtained by conventional breeding and optimization methods or by biotechnological and genetic engineering methods or combinations of these methods, including the transgenic plants and including the plant cultivars which are protectable and non-protectable by plant breeders' rights.

The inventive treatment method can thus also be used for the treatment of genetically modified organisms (GMOs), e.g. plants or seeds. Genetically modified plants (or transgenic plants) are plants in which a heterologous gene has been integrated stably into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing (an)other gene(s) which is/are present in the plant (using for example antisense technology, cosuppression technology or RNAi technology [RNA interference]). A heterologous gene present in the genome is also called a transgene. A transgene that is defined by its specific presence in the plant genome is called a transformation or transgenic event.

Plants and plant cultivars which are preferably treated in accordance with the invention include all plants which have genetic material which imparts particularly advantageous, useful traits to these plants (whether obtained by breeding and/or biotechnological means).

Plants and plant cultivars which can likewise be treated in accordance with the invention are those plants which are resistant to one or more abiotic stress factors. The abiotic stress conditions may include, for example, drought, cold and hot conditions, aridity and lack of water, osmotic stress, waterlogging, elevated soil salinity, elevated exposure to minerals, ozone conditions, strong light conditions, limited availability of nitrogen nutrients, limited availability of phosphorus nutrients or avoidance of shade.

Plants and plant cultivars which can likewise be treated in accordance with the invention are those plants which are characterized by enhanced yield characteristics. Enhanced yield in these plants may be the result of, for example, improved plant physiology, improved plant growth and development, such as water use efficiency, water retention efficiency, improved nitrogen use, enhanced carbon assimilation, improved photosynthesis, increased germination efficiency and accelerated maturation. Yield can also be affected by improved plant architecture (under stress and non-stress conditions), including early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants which can likewise be treated in accordance with the invention are hybrid plants that already express the characteristics of heterosis, or hybrid vigor, which generally results in higher yield, increased vigor, better health and better resistance towards biotic and abiotic stress factors. Such plants are typically produced by crossing an inbred male-sterile parent line (the female parent) with another inbred male-fertile parent line (the male parent). The hybrid seed is typically harvested from the male-sterile plants and sold to growers. Male-sterile plants can sometimes (for example in corn) be produced by detasseling (i.e. mechanical removal of the male reproductive organs or male flowers); however, it is more typical for male sterility to be the result of genetic determinants in the plant genome. In that case, and especially when seed is the desired product to be harvested from the hybrid plants, it is typically beneficial to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmatic male sterility (CMS) have been described, for example, for Brassica species (WO 1992/005251, WO 1995/009910, WO 1998/27806, WO 2005/002324, WO 2006/021972 and U.S. Pat. No. 6,229,072). However, genetic determinants for male sterility can also be located in the nuclear genome. Male-sterile plants can also be obtained by plant biotechnology methods such as genetic engineering. A particularly useful means of obtaining male-sterile plants is described in WO 89/10396, in which, for example, a ribonuclease such as a barnase is selectively expressed in the tapetum cells in the stamens. Fertility can then be restored by expression in the tapetum cells of a ribonuclease inhibitor such as barstar (e.g. WO 1991/002069).

Plants or plant cultivars (obtained by plant biotechnology methods such as genetic engineering) which can likewise be treated in accordance with the invention are herbicide-tolerant plants, i.e. plants which have been made tolerant to one or more given herbicides. Such plants can be obtained either by genetic transformation, or by selection of plants containing a mutation imparting such herbicide tolerance.

Herbicide-tolerant plants are, for example, glyphosate-tolerant plants, i.e. plants which have been made tolerant to the herbicide glyphosate or salts thereof. For example, glyphosate-tolerant plants can be obtained by transforming the plant with a gene which encodes the enzyme 5-enolpyruvylshikimate-3-phosphate synthase (EPSPS). Examples of such EPSPS genes are the AroA gene (mutant CT7) of the bacterium Salmonella typhimurium (Comai et al., Science (1983), 221, 370-371), the CP4 gene of the bacterium Agrobacterium sp. (Barry et al., Curr. Topics Plant Physiol. (1992), 7, 139-145), the genes encoding a petunia EPSPS (Shah et al., Science (1986), 233, 478-481), a tomato EPSPS (Gasser et al., J. Biol. Chem. (1988), 263, 4280-4289) or an Eleusine EPSPS (WO 2001/66704). The gene may also be a mutated EPSPS, as described, for example, in EP-A 0837944, WO 2000/066746, WO 2000/066747 or WO 2002/026995. Glyphosate-tolerant plants can also be obtained by expressing a gene that encodes a glyphosate oxidoreductase enzyme as described in U.S. Pat. No. 5,776,760 and U.S. Pat. No. 5,463,175. Glyphosate-tolerant plants can also be obtained by expressing a gene that encodes a glyphosate acetyltransferase enzyme as described, for example, in WO 2002/036782, WO 2003/092360, WO 2005/012515 and WO 2007/024782. Glyphosate-tolerant plants can also be obtained by selecting plants containing naturally occurring mutations of the abovementioned genes, as described, for example, in WO 2001/024615 or WO 2003/013226.

Other herbicide-resistant plants are, for example, plants that have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from Streptomyces species). Plants expressing an exogenous phosphinothricin acetyltransferase are described, for example, in U.S. Pat. No. 5,561,236; U.S. Pat. No. 5,648,477; U.S. Pat. No. 5,646,024; U.S. Pat. No. 5,273,894; U.S. Pat. No. 5,637,489; U.S. Pat. No. 5,276,268; U.S. Pat. No. 5,739,082; U.S. Pat. No. 5,908,810 and U.S. Pat. No. 7,112,665.

Further herbicide-tolerant plants are also plants that have been made tolerant to the herbicides inhibiting the enzyme hydroxyphenylpyruvate dioxygenase (HPPD). Hydroxyphenylpyruvate dioxygenases are enzymes that catalyze the reaction in which para-hydroxyphenylpyruvate (HPP) is converted to homogentisate. Plants tolerant to HPPD inhibitors can be transformed with a gene encoding a naturally-occurring resistant HPPD enzyme, or a gene encoding a mutated HPPD enzyme according to WO 1996/038567, WO 1999/024585 and WO 1999/024586. Tolerance to HPPD inhibitors can also be obtained by transforming plants with genes encoding certain enzymes enabling the formation of homogentisate despite the inhibition of the native HPPD enzyme by the HPPD inhibitor. Such plants and genes are described in WO 1999/034008 and WO 2002/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928.

Further herbicide-resistant plants are plants that have been made tolerant to acetolactate synthase (ALS) inhibitors. The known ALS inhibitors include, for example, sulfonylurea, imidazolinone, triazolopyrimidines, pyrimidinyl oxy(thio) benzoates and/or sulfonylaminocarbonyltriazolinone herbicides. It is known that different mutations in the ALS enzyme (also known as acetohydroxy acid synthase, AHAS) confer tolerance to different herbicides and groups of herbicides, as described, for example, in Tranel and Wright, Weed Science (2002), 50, 700-712, but also in U.S. Pat. No. 5,605,011, U.S. Pat. No. 5,378,824, U.S. Pat. No. 5,141,870 and U.S. Pat. No. 5,013,659. The production of sulfonylurea-tolerant plants and imidazolinone-tolerant plants has been described in U.S. Pat. No. 5,605,011; U.S. Pat. No. 5,013,659; U.S. Pat. No. 5,141,870; U.S. Pat. No. 5,767,361; U.S. Pat. No. 5,731,180; U.S. Pat. No. 5,304,732; U.S. Pat. No. 4,761,373; U.S. Pat. No. 5,331,107; U.S. Pat. No. 5,928,937; and U.S. Pat. No. 5,378,824; and in the international publication WO 1996/033270. Further imidazolinone-tolerant plants have also been described, for example, in WO 2004/040012, WO 2004/106529, WO 2005/020673, WO 2005/093093, WO 2006/007373, WO 2006/015376, WO 2006/024351 and WO 2006/060634. Further sulfonylurea- and imidazolinone-tolerant plants have also been described, for example in WO 2007/024782.

Further plants tolerant to imidazolinone and/or sulfonylurea can be obtained by induced mutagenesis, by selection in cell cultures in the presence of the herbicide or by mutation breeding, as described, for example, for soybeans in U.S. Pat. No. 5,084,082, for rice in WO 1997/41218, for sugarbeet in U.S. Pat. No. 5,773,702 and WO 1999/057965, for lettuce in U.S. Pat. No. 5,198,599 or for sunflower in WO 2001/065922.

Plants or plant cultivars (obtained by plant biotechnology methods such as genetic engineering) which can also be treated in accordance with the invention are insect-resistant transgenic plants, i.e. plants which have been made resistant to attack by certain target insects. Such plants can be obtained by genetic transformation, or by selection of plants containing a mutation which imparts such insect resistance.

In the present context, the term "insect-resistant transgenic plant" includes any plant containing at least one transgene comprising a coding sequence which encodes the following:

1) an insecticidal crystal protein from *Bacillus thuringiensis* or an insecticidal portion thereof, such as the insecticidal crystal proteins compiled by Crickmore et al., Microbiology and Molecular Biology Reviews (1998), 62, 807-813, updated by Crickmore et al. (2005) in the *Bacillus thuringiensis* toxin nomenclature, (online at: http://www.lifesci.sussex.ac.uk/Home/Neil_Crickmore/Bt/), or insecticidal portions thereof, for example proteins of the Cry protein classes Cry1Ab, Cry1Ac, Cry1F, Cry2Ab, Cry3Ae or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins (Moellenbeck et al., Nat. Biotechnol. (2001), 19, 668-72; Schnepf et al., Applied Environm. Microb. (2006), 71, 1765-1774); or 3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by corn event MON98034 (WO 2007/027777); or 4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in corn events MON863 or MON88017, or the Cry3A protein in corn event MIR 604; or 5) an insecticidal secreted protein from *Bacillus thuringiensis* or *Bacillus cereus*, or an insecticidal portion thereof, such as the vegetative insecticidal proteins (VIPs) listed under the following link, for example proteins from the VIP3Aa protein class: http://www.lifesci.sussex.ac.uk/Home/Neil_Crickmore/Bt/vip.html; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 1994/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the abovementioned classes 1 to 8. In one embodiment, an insect-resistant plant contains more than one transgene encoding a protein of any one of the abovementioned classes 1 to 8, to expand the range of target insect species affected or to delay insect resistance development to the plants, by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:

a. plants which contain a transgene capable of reducing the expression and/or the activity of the poly(ADP-ribose)polymerase (PARP) gene in the plant cells or plants, as described in WO 2000/004173 or EP 04077984.5 or EP 06009836.5;

b. plants which contain a stress tolerance-enhancing transgene capable of reducing the expression and/or the activity of the PARG encoding genes of the plants or plant cells, as described, for example, in WO 2004/090140;

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyl transferase, nicotinamide adenine dinucleotide synthetase or nicotinamide phosphoribosyltransferase, as described, for example, in EP 04077624.7 or WO 2006/133827 or PCT/EP07/002433.

Plants or plant cultivars (obtained by plant biotechnology methods such as genetic engineering) which may also be treated according to the invention show altered quantity, quality and/or storage stability of the harvested product and/or altered properties of specific ingredients of the harvested product such as:

1) Transgenic plants which synthesize a modified starch which is altered with respect to its chemophysical traits, in particular the amylose content or the amylose/amylopectin ratio, the degree of branching, the average chain length, the distribution of the side chains, the viscosity behavior, the gel resistance, the grain size and/or grain morphology of the starch in comparison to the synthesized starch in wild-type plant cells or plants, such that this modified starch is better suited for certain applications. These transgenic plants synthesizing a modified starch are described, for example, in EP 0571427, WO 1995/004826, EP 0719338, WO 1996/15248, WO 1996/19581, WO 1996/27674, WO 1997/11188, WO 1997/26362, WO 1997/32985, WO 1997/42328, WO 1997/44472, WO 1997/45545, WO 1998/27212, WO 1998/40503, WO 99/58688, WO 1999/58690, WO 1999/58654, WO 2000/008184, WO 2000/008185, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 1995/26407, WO 1996/34968, WO 1998/20145, WO 1999/12950, WO 1999/66050, WO 1999/53072, U.S. Pat. No. 6,734,341, WO 2000/11192, WO 1998/22604, WO 1998/32326, WO 2001/98509, WO 2001/98509, WO 2005/002359, U.S. Pat. No. 5,824,790, U.S. Pat. No. 6,013,861, WO 1994/004693, WO 1994/009144, WO 1994/11520, WO 1995/35026 and WO 1997/20936.

2) Transgenic plants which synthesize non-starch carbohydrate polymers or which synthesize non-starch carbohydrate polymers with altered properties in comparison to wild-type plants without genetic modification. Examples are plants producing polyfructose, especially of the inulin and levan type, as described in EP 0663956, WO 1996/001904, WO 1996/021023, WO 1998/039460 and WO 1999/024593, plants producing alpha-1,4-glucans, as described in WO 1995/031553, US 2002/031826, U.S. Pat. No. 6,284,479, U.S. Pat. No. 5,712,107, WO 1997/047806, WO 1997/047807, WO 1997/047808 and WO 2000/14249, plants producing alpha-1,6-branched alpha-1,4-glucans, as described in WO 2000/73422, and plants producing alternan, as described in WO 2000/047727, EP 06077301.7, U.S. Pat. No. 5,908,975 and EP 0728213.

3) Transgenic plants which produce hyaluronan, as for example described in WO 2006/032538, WO 2007/039314, WO 2007/039315, WO 2007/039316, JP 2006/304779 and WO 2005/012529.

Plants or plant cultivars (obtained by plant biotechnology methods such as genetic engineering) which may also be treated according to the invention are plants, such as cotton plants, with altered fiber characteristics. Such plants can be obtained by genetic transformation, or by selection of plants containing a mutation imparting such altered fiber characteristics and include:

a) plants, such as cotton plants, which contain an altered form of cellulose synthase genes, as described in WO 1998/000549;

b) plants, such as cotton plants, which contain an altered form of rsw2 or rsw3 homologous nucleic acids, as described in WO 2004/053219;

c) plants, such as cotton plants, with an increased expression of sucrose phosphate synthase, as described in WO 2001/017333;

d) plants, such as cotton plants, with an increased expression of sucrose synthase, as described in WO 02/45485;

e) plants, such as cotton plants, wherein the timing of the plasmodesmatal gating at the basis of the fiber cell is altered, for example through downregulation of fiber-selective $\beta$-1,3-glucanase, as described in WO 2005/017157;

f) plants, such as cotton plants, which have fibers with altered reactivity, for example through the expression of the N-acetylglucosaminetransferase gene including nodC and chitin synthase genes, as described in WO 2006/136351.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants containing a mutation imparting such altered oil characteristics and include:

a) plants, such as oilseed rape plants, which produce oil having a high oleic acid content, as described, for example, in U.S. Pat. No. 5,969,169, U.S. Pat. No. 5,840,946 or U.S. Pat. No. 6,323,392 or U.S. Pat. No. 6,063,947;

b) plants, such as oilseed rape plants, which produce oil having a low linolenic acid content, as described in U.S. Pat. No. 6,270,828, U.S. Pat. No. 6,169,190 or U.S. Pat. No. 5,965,755;

c) plants, such as oilseed rape plants, which produce oil having a low level of saturated fatty acids, as described, for example, in U.S. Pat. No. 5,434,283.

Particularly useful transgenic plants which may be treated according to the invention are plants which comprise one or more genes which encode one or more toxins and are the transgenic plants which are sold under the following trade names: YIELD GARD® (for example corn, cotton, soybeans), KnockOut® (for example corn), BiteGard® (for example corn), BT-Xtra® (for example corn), StarLink® (for example corn), Bollgard® (cotton), Nucotn® (cotton), Nucotn 33B® (cotton), NatureGard® (for example corn), Protecta® and NewLeaf® (potato). Examples of herbicide-tolerant plants which should be mentioned are corn varieties, cotton varieties and soybean varieties which are available under the following trade names: Roundup Ready® (tolerance to glyphosate, for example corn, cotton, soybeans), Liberty Link® (tolerance to phosphinothricin, for example oilseed rape), IMI® (tolerance to imidazolinone) and SOS® (tolerance to sulfonylurea, for example corn). Herbicide-resistant plants (plants bred in a conventional manner for herbicide tolerance) which should be mentioned include the varieties sold under the Clearfield® name (for example corn).

Particularly useful transgenic plants which may be treated according to the invention are plants containing transformation events, or a combination of transformation events, and that are listed for example in the databases for various national or regional regulatory agencies.

The derivatives of (1-cyanocyclopropyl)phenylphosphinic acid or esters thereof, of the formula (I), and/or salts thereof, of the formula (II), to be used in accordance with the invention can be converted to customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active ingredient, synthetic substances impregnated with active ingredient, fertilizers, and also microencapsulations in polymeric substances. In the context of the present invention, it is especially preferred when the derivatives of (1-cyanocyclopropyl)phenylphosphinic acid or esters thereof, of the formula (I), and/or salts thereof, of the formula (II), are used in the form of a spray formulation.

The present invention therefore additionally also relates to a spray formulation for enhancing the resistance of plants to abiotic stress, preferably to drought stress. A spray formulation is described in detail hereinafter:

The formulations for spray application are produced in a known manner, for example by mixing the derivatives of (1-cyanocyclopropyl)phenylphosphinic acid or esters thereof, of the formula (I), and/or salts thereof, of the formula (II), for use in accordance with the invention with extenders, i.e. liquid solvents and/or solid carriers, optionally with use of surfactants, i.e. emulsifiers and/or dispersants and/or foam formers. Further customary additives, for example customary extenders and solvents or diluents, dyes, wetting agents, dispersants, emulsifiers, antifoams, preservatives, secondary thickeners, stickers, gibberellins and also water, can optionally also be used. The formulations are produced either in suitable plants or else before or during application.

The auxiliaries used may be those substances which are suitable for imparting, to the composition itself and/or to preparations derived therefrom (for example spray liquors), particular properties such as particular technical properties and/or else special biological properties. Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethyl sulfoxide).

If the extender used is water, it is also possible to use, for example, organic solvents as auxiliary solvents. Useful liquid solvents essentially include: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethyl sulfoxide, and also water.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Useful wetting agents which may be present in the formulations usable in accordance with the invention are all substances which promote wetting and which are conventionally used for the formulation of active agrochemical ingredients. Preference is given to using alkyl naphthalenesulfonates, such as diisopropyl or diisobutyl naphthalenesulfonates.

Useful dispersants and/or emulsifiers which may be present in the formulations usable in accordance with the invention are all nonionic, anionic and cationic dispersants conventionally used for the formulation of active agrochemical ingredients. Usable with preference are nonionic or anionic dispersants or mixtures of nonionic or anionic dispersants. Suitable nonionic dispersants are especially ethylene oxide/propylene oxide block polymers, alkylphenol polyglycol ethers and tristyrylphenol polyglycol ether, and the phosphated or sulfated derivatives thereof.

Suitable anionic dispersants are especially lignosulfonates, polyacrylic acid salts and arylsulfonate/formaldehyde condensates.

Antifoams which may be present in the formulations usable in accordance with the invention are all foam-inhibiting substances conventionally used for the formulation of active agrochemical ingredients. Silicone antifoams and magnesium stearate can be used with preference.

Preservatives which may be present in the formulations usable in accordance with the invention are all substances usable for such purposes in agrochemical compositions. Examples include dichlorophene and benzyl alcohol hemiformal.

Secondary thickeners which may be present in the formulations usable in accordance with the invention are all substances usable for such purposes in agrochemical compositions. Preferred examples include cellulose derivatives, acrylic acid derivatives, xanthan, modified clays and finely divided silica.

Stickers which may be present in the formulations usable in accordance with the invention include all customary binders usable in seed-dressing products. Preferred examples include polyvinylpyrrolidone, polyvinyl acetate, polyvinyl alcohol and tylose. Gibberellins which may be present in the formulations usable in accordance with the invention may preferably be gibberellins A1, A3 (=gibberellic acid), A4 and A7; particular preference is given to using gibberellic acid. The gibberellins are known (cf. R. Wegler "Chemie der Pflanzenschutz- and Schädlingsbekämpfungsmittel" [Chemistry of the Crop Protection Compositions and Pesticides], vol. 2, Springer Verlag, 1970, p. 401-412).

Further additives may be fragrances, mineral or vegetable, optionally modified oils, waxes and nutrients (including trace nutrients), such as salts of iron, manganese, boron, copper, cobalt, molybdenum and zinc. Additionally present may be stabilizers, such as cold stabilizers, antioxidants, light stabilizers or other agents which improve chemical and/or physical stability.

The formulations comprise generally between 0.01 and 98% by weight, preferably between 0.5 and 90% of one or more of the derivatives of (1-cyanocyclopropyl)phenylphosphinic acid or esters thereof, of the formula (I), and/or one or more salts, of the formula (II).

Derivatives of (1-cyanocyclopropyl)phenylphosphinic acid or esters thereof, of the formula (I), and/or salts thereof, of the formula (II), may be present in commercially available formulations and also in the use forms, prepared from these formulations, as a mixture with other active compounds, such as insecticides, attractants, sterilants, bactericides, acaricides, nematicides, fungicides, growth regulators, herbicides, safeners, fertilizers or semiochemicals.

In addition, the described positive effect of the derivatives of (1-cyanocyclopropyl)phenylphosphinic acid or esters thereof, of the formula (I), and/or salts thereof, of the formula (II), on the plants' own defenses can be supported by an additional treatment with active insecticidal, fungicidal or bactericidal ingredients.

Preferred times for the application of one or more derivatives of (1-cyanocyclopropyl)phenylphosphinic acid or esters thereof, of the formula (I), and/or one or more salts, of the formula (II), for enhancing resistance to abiotic stress, preferably to drought stress, are treatments of the soil, stems and/or leaves with the approved application rates.

The derivatives of (1-cyanocyclopropyl)phenylphosphinic acid or esters thereof, of the formula (I), and/or salts thereof, of the formula (II), may generally additionally be present in their commercial formulations and in the use forms prepared from these formulations in mixtures with other active ingredients, such as insecticides, attractants, sterilants, acaricides, nematicides, fungicides, growth regulators, substances which influence plant maturity, safeners or herbicides. Particularly favorable mixing partners are, for example, the active ingredients of the different classes, specified below in groups, without any preference resulting from the sequence thereof:

Fungicides:

F1) nucleic acid synthesis inhibitors, for example benalaxyl, benalaxyl-M, bupirimate, chiralaxyl, clozylacon, dimethirimol, ethirimol, furalaxyl, hymexazole, metalaxyl, metalaxyl-M, ofurace, oxadixyl, oxolinic acid;

F2) mitosis and cell division inhibitors, for example benomyl, carbendazim, diethofencarb, fuberidazole, fluopicolid, pencycuron, thiabendazole, thiophanate-methyl, zoxamide and chloro-7-(4-methylpiperidin-1-yl)-6-(2,4,6-trifluorophenyl)[1,2,4]triazolo[1,5-a]pyrimidine;

F3) respiratory chain complex I/II inhibitors, for example diflumetorim, bixafen, boscalid, carboxin, diflumethorim, fenfuram, fluopyram, flutolanil, furametpyr, mepronil, oxycarboxin, penflufen, penthiopyrad, thifluzamid, N-[2-(1,3-dimethylbutyl)phenyl]-5-fluoro-1,3-dimethyl-1H-pyrazole-4-carboxamide, isopyrazam, sedaxan, 3-(difluoromethyl)-1-methyl-N-(3',4',5'-trifluorobiphenyl-2-yl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide and corresponding salts;

F4) respiratory chain complex III inhibitors, for example amisulbrom, azoxystrobin, cyazofamid, dimoxystrobin, enestrobin, famoxadon, fenamidon, fluoxastrobin, kresoxim-methyl, metominostrobin, orysastrobin, pyraclostrobin, pyribencarb, picoxystrobin, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(ethoxyimino)-N-methyl-2-(2-{[({(1E)-1-[3-(trifluoromethyl)phenyl]ethylidene}amino)oxy]methyl}phenyl)ethanamide and corresponding salts, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyhethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-[3-(trifluoromethyl)phenyl]ethylidene}amino)oxy]methyl}phenyl)-2,4-dihydro-3H-1,2,4-triazol-3-one, 2-methyl{2-[({cyclopropyl[(4-methoxyphenyl)imino]methyl}sulfanyl)methyl]phenyl}-3-methoxyacrylate, N-(3-ethyl-3,5,5-trimethylcyclohexyl)-3-(formylamino)-2-hydroxybenzamide and corresponding salts;

F5) decouplers, for example dinocap, fluazinam;

F6) ATP production inhibitors, for example fentin acetate, fentin chloride, fentin hydroxide, silthiofam F7) amino acid and protein biosynthesis inhibitors, for example andoprim, blasticidin-S, cyprodinil, kasugamycin, kasugamycin hydrochloride hydrate, mepanipyrim, pyrimethanil F8) signal transduction inhibitors, for example fenpiclonil, fludioxonil, quinoxyfen F9) lipid and membrane synthesis inhibitors, for example chlozolinate, iprodione, procymidone, vinclozolin, ampropylfos, potassium-ampropylfos, edifenphos, iprobenfos (IBP), isoprothiolane, pyrazophos, tolclofos-methyl, biphenyl, iodocarb, propamocarb, propamocarb hydrochloride F10) ergosterol biosynthesis inhibitors, for example fenhexamid, azaconazole, bitertanol, bromuconazole, diclobutrazole, difenoconazole, diniconazole, diniconazole-M, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, spiroxamine, tebuconazole, triadimefon, triadimenol, triticonazole, uniconazole, voriconazole, imazalil, imazalil sulfate, oxpoconazole, fenarimol, flurprimidol, nuarimol, pyrifenox, triforin, pefurazoat, prochloraz, triflumizole, viniconazole, aldimorph, dodemorph, dodemorph acetate, fenpropimorph, tridemorph, fenpropidin, naftifin, pyributicarb, terbinafin, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-{1-[(4-methoxyphenoxy)methyl]-2,2-dimethylpropyl}-1H-imidazole-1-carbothioate;

F11) cell wall synthesis inhibitors, for example benthiavalicarb, bialaphos, dimethomorph, flumorph, iprovalicarb, polyoxins, polyoxorim, validamycin A F12) melanine biosynthesis inhibitors, for example capropamide, diclocymet, fenoxanil, phthalide, pyroquilon, tricyclazole F13) resistance induction, for example acibenzolar-S-methyl, probenazole, tiadinil, isotianil F14) multisite, for example captafol, captan, chlorothalonil, copper salts such as: copper hydroxide, copper naphthenate, copper oxychloride, copper sulfate, copper oxide, oxine-copper and Bordeaux mixture, dichlofluanid, dithianon, dodine, dodine free base, ferbam, folpet, fluorofolpet, guazatine, guazatine acetate, iminoctadine, iminoctadine albesilate, iminoctadine triacetate, mancopper, mancozeb, maneb, metiram, metiram zinc, propineb, sulfur and sulfur preparations containing calcium polysulfide, thiram, tolylfluanid, zineb, ziram F15) unknown mechanism, for example amibromdol, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methyl sulfate, diphenylamine, ethaboxam, ferimzone, flumetover, flusulfamide, fluopicolide, fluoroimide, fosatyl-Al, hexachlorobenzene, 8-hydroxyquinoline sulfate, iprodione, irumamycin, isotianil, methasulfocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosine-sodium, proquinazid, pyrrolnitrin, quintozene, tecloftalam, tecnazene, triazoxide, trichlamide, zarilamid and 2,3,5,6-tetrachloro-4-(methylsulfonyl)pyridine, N-(4-chloro-2-nitrophenyl)-N-ethyl-4-methylbenzenesulfonamide, 2-amino-4-methyl-N-phenyl-5-thiazolecarboxamide, 2-chloro-N-(2,3-dihydro-1,1,3-trimethyl-1H-inden-4-yl)-3-pyridinecarboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)

phenyl]ethylidene]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridinedicarbonitrile, methyl 2-[[[cyclopropyl[(4-methoxyphenyhimino]methyl]thio]methyl].alpha.-(methoxymethylene)benzacetate, 4-chloro-alpha-propynyloxy-N-[2-[3-methoxy-4-(2-propynyloxy)phenyl]ethyl]benzacetamide, (2S)—N-[2-[4-[[3-(4-chlorophenyl)-2-propynyl]oxy]-3-methoxyphenyl]ethyl]-3-methyl-2-[(methylsulfonyl)amino]butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl)[1,2,4]triazolo[1,5-a]pyrimidine-7-amine, N-[1-(5-bromo-3-chloropyridin-2-yhethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N—{(Z)-[(cyclopropylmethoxy)imino][6-(difluoromethoxy)-2,3-difluorophenyl]methyl}-2-benzacetamide, N-(3-ethyl-3,5,5-trimethylcyclohexyl)-3-formylamino-2-hydroxybenzamide, 2-[[[[1-[3-(1-fluoro-2-phenylethyl)oxy]phenyl]ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-methoxy-3-pyridinyl)cyclopropanecarboxamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chloro-2-methylphenoxy)-5-fluoropyrimidin-4-yl]oxy}phenyl)-2-(methoxyimino)-N-methylacetamide.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulfate and other copper preparations.

Insecticides/acaricides/nematicides:

I1) acetylcholine esterase (AChE) inhibitors, a) from the substance group of the carbamates, for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, fenoxycarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate, b) from the group of the organophosphates, for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulfone, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion I2) sodium channel modulators/voltage-dependent sodium channel blockers, a) from the group of the pyrethroids, for example acrinathrin, allethrin (d-cis-trans, d-trans), beta-cyfluthrin, bifenthrin, bioallethrin, bioallethrin-S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, eflusilanate, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, pyrethrin, resmethrin, RU 15525, silafluofen, tau-fluvalinate, tefluthrin, terallethrin, tetramethrin (1R isomer), tralomethrin, transfluthrin, ZXI 8901, pyrethrins (pyrethrum), b) DDT, c) oxadiazines, for example indoxacarb, d) semicarbazones, for example metaflumizone (BAS3201)

I3) acetylcholine receptor agonists/antagonists, a) from the group of the chloronicotinyls, for example acetamiprid, AKD 1022, clothianidin, dinotefuran, imidacloprid, imidaclothiz, nitenpyram, nithiazine, thiacloprid, thiamethoxam, b) nicotine, bensultap, cartap;

I4) acetylcholine receptor modulators from the group of the spinosyns, for example spinosad I5) GABA-gated chloride channel antagonists, a) from the group of the organochlorines, for example camphechlor, chlordane, endosulfan, gamma-HCH, HCH, heptachlor, lindane, methoxychlor, b) fiproles, for example acetoprole, ethiprole, fipronil, pyrafluprole, pyriprole, vaniliprole;

I6) chloride channel activators, for example abamectin, emamectin, emamectin benzoate, ivermectin, lepimectin, milbemycin;

I7) juvenile hormone mimetics, for example diofenolan, epofenonane, fenoxycarb, hydroprene, kinoprene, methoprene, pyriproxifen, triprene;

I8) ecdysone agonists/disruptors, for example chromafenozide, halofenozide, methoxyfenozide, tebufenozide;

I9) chitin biosynthesis inhibitors, for example bistrifluron, chlofluazuron, diflubenzuron, fluazuron, flucycloxuron, flufenoxuron, hexaflumuron, lufenuron, novaluron, noviflumuron, penfluron, teflubenzuron, triflumuron, buprofezin, cyromazine;

I10) inhibitors of oxidative phosphorylation, a) ATP disruptors, for example diafenthiuron, b) organotin compounds, for example azocyclotin, cyhexatin, fenbutatin oxide;

I11) decouplers of oxidative phosphorylation by interruption of the H-proton gradient, a) from the group of the pyrroles, for example chlorfenapyr, b) from the class of the dinitrophenols, for example binapacyr, dinobuton, dinocap, DNOC, meptyldinocap;

I12) site I electron transport inhibitors, for example METIs, especially, as examples, fenazaquin, fenpyroximate, pyrimidifen, pyridaben, tebufenpyrad, tolfenpyrad or else hydramethylnon, dicofol I13) site II electron transport inhibitors, for example rotenone I14) site III electron transport inhibitors, for example acequinocyl, fluacrypyrim I15) microbial disruptors of the insect gut membrane, for example *Bacillus thuringiensis* strains I16) lipid synthesis inhibitors, a) from the group of the tetronic acids, for example spirodiclofen, spiromesifen, b) from the class of the tetramic acids, for example spirotetramat, cis-3-(2,5-dimethylphenyl)-4-hydroxy-8-methoxy-1-azaspiro[4.5]dec-3-en-2-one I17) octopaminergic agonists, for example amitraz I18) inhibitors of magnesium-stimulated ATPase, for example propargite I19) nereistoxin analogs, for example thiocyclam hydrogen oxalate, thiosultap-sodium I20) ryanodine receptor agonists, a) from the group of the benzenedicarboxamides, for example flubendiamide, b) from the group of the anthranilamides, for example rynaxypyr (3-bromo-N-{4-chloro-2-methyl-6-[(methylamino)carbonyl]phenyl}-1-(3-chloropyridin-2-yl)-1H-pyrazole-5-carboxamide), cyazypyr (ISO-proposed) (3-bromo-N-{4-cyano-2-methyl-6-[(methylamino)carbonyl]phenyl}-1-(3-chloropyridin-2-yl)-1H-pyrazole-5-carboxamide) (known from WO 2004067528)

I21) biologics, hormones or pheromones, for example azadirachtin, *Bacillus* spec., *Beauveria* spec., codlemone, *Metarrhizium* spec., *Paecilomyces* spec., thuringiensin, *Verticillium* spec.

I22) active ingredients with unknown or nonspecific mechanisms of action, a) fumigants, for example aluminum phosphide, methyl bromide, sulfuryl fluoride, b) antifeedants, for example cryolite, flonicamid, pymetrozine, c) mite growth inhibitors, for example clofentezine, etoxazole, hexythiazox, d) amidoflumet, benclothiaz, benzoximate, bifenazate, bromopropylate, buprofezin, chinomethionat, chlorodimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnon, japonilure, metoxadiazone, petroleum, piperonyl butoxide, potassium oleate, pyridalyl, sulfluramid, tetradifon, tetrasul, triarathene, verbutin or lepimectin Safeners are preferably selected from the group consisting of:

S1) compounds of the formula (S1)

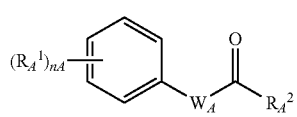

(S1)

where the symbols and indices are each defined as follows:

$n_A$ is a natural number from 0 to 5, preferably from 0 to 3;

$R_A^1$ is halogen, $(C_1\text{-}C_4)$alkyl, $(C_1\text{-}C_4)$alkoxy, nitro or $(C_1\text{-}C_4)$haloalkyl;

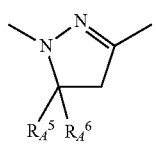

$(W_A^1)$

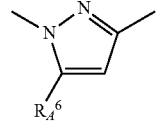

$(W_A^2)$

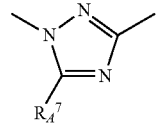

$(W_A^3)$

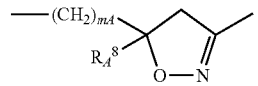

$(W_A^4)$ $W_A$ is an unsubstituted or substituted divalent heterocyclic radical from the group of the partially unsaturated or aromatic five-membered heterocycles having 1 to 3 ring heteroatoms of the N or O type, where at least one nitrogen atom and at most one oxygen atom is present in the ring, preferably a radical from the group of $(W_A^1)$ to $(W_A^4)$;

$m_A$ is 0 or 1;

$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group of O and S, which is joined to the carbonyl group in (S1) via the nitrogen atom and is unsubstituted or substituted by radicals from the group of $(C_1\text{-}C_4)$alkyl, $(C_1\text{-}C_4)$alkoxy or optionally substituted phenyl, preferably a radical of the formula $OR_A^3$, $NHR_A^4$ or $N(CH_3)_2$, especially of the formula $OR_A^3$;

$R_A^3$ is hydrogen or an unsubstituted or substituted aliphatic hydrocarbyl radical preferably having a total of 1 to 18 carbon atoms;

$R_A^4$ is hydrogen, $(C_1\text{-}C_6)$alkyl, $(C_1\text{-}C_6)$alkoxy or substituted or unsubstituted phenyl;

$R_A^5$ is H, $(C_1\text{-}C_8)$alkyl, $(C_1\text{-}C_8)$haloalkyl, $(C_1\text{-}C_4)$alkoxy$(C_1\text{-}C_8)$alkyl, cyano or $COOR_A^9$ in which $R_A^9$ is hydrogen, $(C_1\text{-}C_8)$alkyl, $(C_1\text{-}C_8)$haloalkyl, $(C_1\text{-}C_4)$alkoxy$(C_1\text{-}C_4)$alkyl, $(C_1\text{-}C_6)$hydroxyalkyl, $(C_3\text{-}C_{12})$cycloalkyl or tri-$(C_1\text{-}C_4)$-alkylsilyl;

$R_A^6$, $R_A^7$, $R_A^8$ are the same or different and are each hydrogen, $(C_1\text{-}C_8)$alkyl, $(C_1\text{-}C_8)$haloalkyl, $(C_3\text{-}C_{12})$cycloalkyl or substituted or unsubstituted phenyl;

preferably:

a) compounds of the dichlorophenylpyrazoline-3-carboxylic acid ($S1^a$) type, preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds as described in WO-A-91/07874;

b) derivatives of dichlorophenylpyrazolecarboxylic acid ($S1^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds as described in EP-A-333 131 and EP-A-269 806;

c) derivatives of 1,5-diphenylpyrazole-3-carboxylic acid ($S1^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds as described, for example, in EP-A-268554;

d) compounds of the triazolecarboxylic acid type (S1$^d$), preferably compounds such as fenchlorazole(-ethyl ester), i.e. ethyl 1-(2,4-dichlorophenyl)-5-trichloromethyl-(1H)-1,2,4-triazole-3-carboxylate (S1-7), and related compounds as described in EP-A-174 562 and EP-A-346 620;

e) compounds of the 5-benzyl- or 5-phenyl-2-isoxazoline-3-carboxylic acid or of the 5,5-diphenyl-2-isoxazoline-3-carboxylic acid type (S1$^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds as described in WO-A-91/08202, or 5,5-diphenyl-2-isoxazolinecarboxylic acid (S1-10) or ethyl 5,5-diphenyl-2-isoxazoline-3-carboxylate (S1-11) ("isoxadifen-ethyl") or n-propyl 5,5-diphenyl-2-isoxazoline-3-carboxylate (S1-12) or ethyl 5-(4-fluorophenyl)-5-phenyl-2-isoxazoline-3-carboxylate (S1-13), as described in patent application WO-A-95/07897.

S2) Quinoline derivatives of the formula (S2)

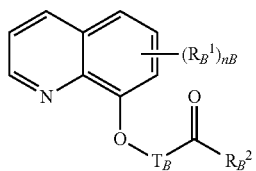

where the symbols and indices are each defined as follows:
$R_B^1$ is halogen, $(C_1$-$C_4)$alkyl, $(C_1$-$C_4)$alkoxy, nitro or $(C_1$-$C_4)$haloalkyl;
$n_B$ is a natural number from 0 to 5, preferably from 0 to 3;
$R_B^2$ is $OR_B^3$, $SR_B^3$ or $NR_B^3R_B^4$ or a saturated or unsaturated 3- to 7-membered heterocycle having at least one nitrogen atom and up to 3 heteroatoms, preferably from the group of O and S, which is joined to the carbonyl group in (S2) via the nitrogen atom and is unsubstituted or substituted by radicals from the group of $(C_1$-$C_4)$alkyl, $(C_1$-$C_4)$alkoxy or optionally substituted phenyl, preferably a radical of the formula $OR_B^3$, $NHR_B^4$ or $N(CH_3)_2$, especially of the formula $OR_B^3$;
$R_B^3$ is hydrogen or an unsubstituted or substituted aliphatic hydrocarbyl radical preferably having a total of 1 to 18 carbon atoms;
$R_B^4$ is hydrogen, $(C_1$-$C_6)$alkyl, $(C_1$-$C_6)$alkoxy or substituted or unsubstituted phenyl;
$T_B$ is a $(C_1$ or $C_2)$-alkanediyl chain which is unsubstituted or substituted by one or two $(C_1$-$C_4)$alkyl radicals or by $[(C_1$-$C_3)$-alkoxy]carbonyl;
preferably:

a) compounds of the 8-quinolinoxyacetic acid type (S2$^a$), preferably 1-methylhexyl(5-chloro-8-quinolinoxy)acetate ("cloquintocet-mexyl") (S2-1), 1,3-dimethylbut-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl(5-chloro-8-quinolinoxy)acetate (S2-5), methyl(5-chloro-8-quinolinoxy)acetate (S2-6), allyl(5-chloro-8-quinolinoxy)acetate (S2-7), 2-(2-propylideneiminoxy)-1-ethyl(5-chloro-8-quinolinoxy)acetate (S2-8), 2-oxoprop-1-yl (5-chloro-8-quinolinoxy)acetate (S2-9) and related compounds, as described in EP-A-86 750, EP-A-94 349 and EP-A-191 736 or EP-A-0 492 366, and also (5-chloro-8-quinolinoxy)acetic acid (S2-10), hydrates and salts thereof, for example the lithium, sodium, potassium, calcium, magnesium, aluminum, iron, ammonium, quaternary ammonium, sulfonium or phosphonium salts thereof, as described in WO-A-2002/34048;

b) compounds of the (5-chloro-8-quinolinoxy)malonic acid type (S2$^b$), preferably compounds such as diethyl(5-chloro-8-quinolinoxy)malonate, diallyl (5-chloro-8-quinolinoxy)malonate, methyl ethyl(5-chloro-8-quinolinoxy)malonate and related compounds, as described in EP-A-0 582 198.

S3) Compounds of the formula (S3)

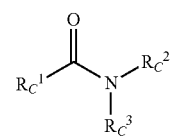

where the symbols and indices are each defined as follows:
$R_C^1$ is $(C_1$-$C_4)$alkyl, $(C_1$-$C_4)$haloalkyl, $(C_2$-$C_4)$alkenyl, $(C_2$-$C_4)$haloalkenyl, $(C_3$-$C_7)$cycloalkyl, preferably dichloromethyl;
$R_C^2$, $R_C^3$ are the same or different and are each hydrogen, $(C_1$-$C_4)$alkyl, $(C_2$-$C_4)$alkenyl, $(C_2$-$C_4)$alkynyl, $(C_1$-$C_4)$haloalkyl, $(C_2$-$C_4)$haloalkenyl, $(C_1$-$C_4)$alkylcarbamoyl-$(C_1$-$C_4)$alkyl, $(C_2$-$C_4)$alkenylcarbamoyl$(C_1$-$C_4)$alkyl, $(C_1$-$C_4)$alkoxy$(C_1$-$C_4)$alkyl, dioxolanyl$(C_1$-$C_4)$alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring; preferably: active ingredients of the dichloroacetamide type, which are frequently used as pre-emergence safeners (soil-acting safeners), for example "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl]dichloroacetamide) from PPG Industries (S3-5), "DKA-24" (N-allyl-N-[(allylaminocarbonyl)methyl]dichloroacetamide) from Sagro-Chem (S3-6), "AD-67" or "MON 4660" (3-dichloroacetyl-1-oxa-3-azaspiro[4,5]decane) from Nitrokemia or Monsanto (S3-7), "TI-35" (1-dichloroacetylazepane) from TRI-Chemical RT (S3-8), "diclonon" (dicyclonone) or "BAS145138" or "LAB145138" (S3-9) ((RS)-1-dichloroacetyl-3,3,8a-trimethylperhydropyrrolo[1,2-a]pyrimidin-6-one) from BASF, "furilazole" or "MON 13900" ((RS)-3-dichloroacetyl-5-(2-furyl)-2,2-dimethyloxazolidine) (S3-10); and the (R) isomer thereof (S3-11).

S4) N-Acylsulfonamides of the formula (S4) and salts thereof

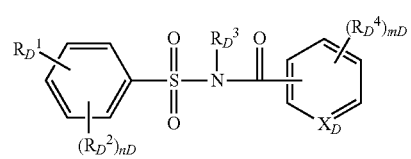

in which the symbols and indices are each defined as follows:

$X_D$ is CH or N;

$R_D^1$ is CO—$NR_D^5 R_D^6$ or NHCO—$R_D^7$;

$R_D^2$ is halogen, $(C_1\text{-}C_4)$haloalkyl, $(C_1\text{-}C_4)$haloalkoxy, nitro, $(C_1\text{-}C_4)$alkyl, $(C_1\text{-}C_4)$alkoxy, $(C_1\text{-}C_4)$alkylsulfonyl, $(C_1\text{-}C_4)$alkoxycarbonyl or $(C_1\text{-}C_4)$alkylcarbonyl;

$R_D^3$ is hydrogen, $(C_1\text{-}C_4)$alkyl, $(C_2\text{-}C_4)$alkenyl or $(C_2\text{-}C_4)$alkynyl;

$R_D^4$ is halogen, nitro, $(C_1\text{-}C_4)$alkyl, $(C_1\text{-}C_4)$haloalkyl, $(C_1\text{-}C_4)$haloalkoxy, $(C_3\text{-}C_6)$cycloalkyl, phenyl, $(C_1\text{-}C_4)$alkoxy, cyano, $(C_1\text{-}C_4)$alkylthio, $(C_1\text{-}C_4)$alkylsulfinyl, $(C_1\text{-}C_4)$alkylsulfonyl, $(C_1\text{-}C_4)$alkoxycarbonyl or $(C_1\text{-}C_4)$alkylcarbonyl;

$R_D^5$ is hydrogen, $(C_1\text{-}C_6)$alkyl, $(C_3\text{-}C_6)$cycloalkyl, $(C_2\text{-}C_6)$alkenyl, $(C_2\text{-}C_6)$alkynyl, $(C_5\text{-}C_6)$cycloalkenyl, phenyl or 3- to 6-membered heterocyclyl containing $v_D$ heteroatoms from the group of nitrogen, oxygen and sulfur, where the seven latter radicals are substituted by $v_D$ substituents from the group of halogen, $(C_1\text{-}C_6)$alkoxy, $(C_1\text{-}C_6)$haloalkoxy, $(C_1\text{-}C_2)$alkylsulfinyl, $(C_1\text{-}C_2)$alkylsulfonyl, $(C_3\text{-}C_6)$cycloalkyl, $(C_1\text{-}C_4)$alkoxycarbonyl, $(C_1\text{-}C_4)$alkylcarbonyl and phenyl and, in the case of cyclic radicals, also $(C_1\text{-}C_4)$alkyl and $(C_1\text{-}C_4)$haloalkyl;

$R_D^6$ is hydrogen, $(C_1\text{-}C_6)$alkyl, $(C_2\text{-}C_6)$alkenyl or $(C_2\text{-}C_6)$alkynyl, where the three latter radicals are substituted by $v_D$ radicals from the group of halogen, hydroxy, $(C_1\text{-}C_4)$alkyl, $(C_1\text{-}C_4)$alkoxy and $(C_1\text{-}C_4)$alkylthio, or $R_D^5$ and $R_D^6$ together with the nitrogen atom which bears them form a pyrrolidinyl or piperidinyl radical;

$R_D^7$ is hydrogen, $(C_1\text{-}C_4)$alkylamino, di$(C_1\text{-}C_4)$alkylamino, $(C_1\text{-}C_6)$alkyl, $(C_3\text{-}C_6)$cycloalkyl, where the 2 latter radicals are substituted by $v_D$ substituents from the group of halogen, $(C_1\text{-}C_4)$alkoxy, $(C_1\text{-}C_6)$haloalkoxy and $(C_1\text{-}C_4)$alkylthio and, in the case of cyclic radicals, also $(C_1\text{-}C_4)$alkyl and $(C_1\text{-}C_4)$haloalkyl;

$n_D$ is 0, 1 or 2;

$m_D$ is 1 or 2;

$v_D$ is 0, 1, 2 or 3;

among these, preference is given to compounds of the N-acylsulfonamide type, for example of the formula (S4$^a$) below, which are known, for example, from WO-A-97/45016

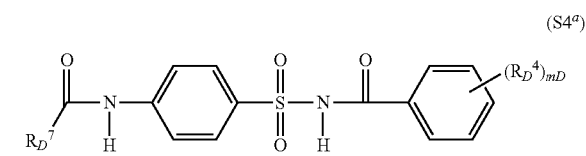

(S4$^a$)

in which $R_D^7$ is $(C_1\text{-}C_6)$alkyl, $(C_3\text{-}C_6)$cycloalkyl, where the 2 latter radicals are substituted by $v_D$ substituents from the group of halogen, $(C_1\text{-}C_4)$alkoxy, $(C_1\text{-}C_6)$haloalkoxy and $(C_1\text{-}C_4)$alkylthio and, in the case of cyclic radicals, also $(C_1\text{-}C_4)$alkyl and $(C_1\text{-}C_4)$haloalkyl;

$R_D^4$ is halogen, $(C_1\text{-}C_4)$alkyl, $(C_1\text{-}C_4)$alkoxy, $CF_3$;

$m_D$ is 1 or 2;

$v_D$ is 0, 1, 2 or 3;

and also to acylsulfamoylbenzamides, for example of the formula (S4$^b$) below, which are known, for example, from WO-A-99/16744,

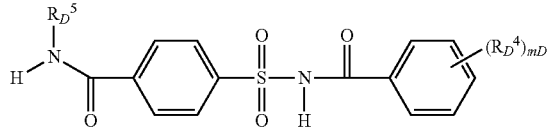

(S4$^b$)

for example those in which $R_D^5$=cyclopropyl and $(R_D^4)$=2-OMe ("cyprosulfamide", S4-1), $R_D^5$=cyclopropyl and $(R_D^4)$=5-Cl-2-OMe (S4-2), $R_D^5$=ethyl and $(R_D^4)$=2-OMe (S4-3), $R_D^5$=isopropyl and $(R_D^4)$=5-Cl-2-OMe (S4-4) and $R_D^5$=isopropyl and $(R_D^4)$=2-OMe (S4-5)

and to compounds of the N-acylsulfamoylphenylurea type, of the formula (S4$^c$), which are known, for example, from EP-A-365484,

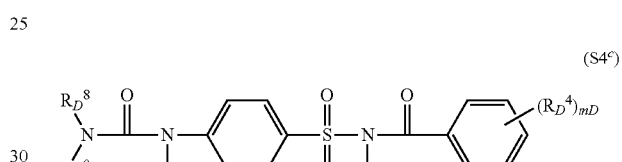

(S4$^c$)

in which $R_D^8$ and $R_D^9$ are each independently hydrogen, $(C_1\text{-}C_8)$alkyl, $(C_3\text{-}C_8)$cycloalkyl, $(C_3\text{-}C_6)$alkenyl, $(C_3\text{-}C_6)$alkynyl, $R_D^4$ is halogen, $(C_1\text{-}C_4)$alkyl, $(C_1\text{-}C_4)$alkoxy, $CF_3$, $m_D$ is 1 or 2;

for example

1-[4-(N-2-methoxybenzoylsulfamoyl)phenyl]-3-methylurea,

1-[4-(N-2-methoxybenzoylsulfamoyl)phenyl]-3,3-dimethylurea,

1-[4-(N-4,5-dimethylbenzoylsulfamoyl)phenyl]-3-methylurea.

S5) Active ingredients from the class of the hydroxyaromatics and the aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 2,4-dichlorocinnamic acid, as described in WO-A-2004/084631, WO-A-2005/015994, WO-A-2005/016001.

S6) Active ingredients from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as described in WO-A-2005/112630.

S7) Compounds of the formula (S7), as described in WO-A-1998/38856,

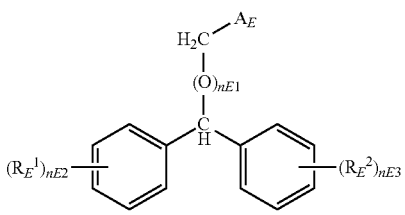
(S7)

in which the symbols and indices are each defined as follows:
$R_E^1$, $R_E^2$ are each independently halogen, $(C_1-C_4)$alkyl, $(C_1-C_4)$alkoxy, $(C_1-C_4)$haloalkyl, $(C_1-C_4)$alkylamino, di$(C_1-C_4)$alkylamino, nitro;
$A_E$ is $COOR_E^3$ or $COSR_E^4$
$R_E^3$, $R_E^4$ are each independently hydrogen, $(C_1-C_4)$alkyl, $(C_2-C_6)$alkenyl, $(C_2-C_4)$alkynyl, cyanoalkyl, $(C_1-C_4)$haloalkyl, phenyl, nitrophenyl, benzyl, halobenzyl, pyridinylalkyl and alkylammonium,
$n_E^1$ is 0 or 1
$n_E^2$, $n_E^3$ are each independently 0, 1 or 2,
preferably di phenylmethoxyacetic acid, ethyl diphenylmethoxyacetate, methyl diphenylmethoxyacetate (CAS reg. no. 41858-19-9) (S7-1).
S8) Compounds of the formula (S8), as described in WO-A-98/27049,

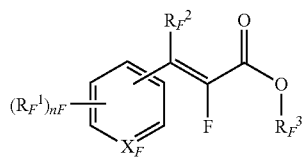
(S8)

in which
$X_F$ is CH or N,
$n_F$ in the case that $X_F$=N is an integer from 0 to 4 and in the case that $X_F$=CH is an integer from 0 to 5,
$R_F^1$ is halogen, $(C_1-C_4)$alkyl, $(C_1-C_4)$haloalkyl, $(C_1-C_4)$alkoxy, $(C_1-C_4)$haloalkoxy, nitro, $(C_1-C_4)$alkylthio, $(C_1-C_4)$alkylsulfonyl, $(C_1-C_4)$alkoxycarbonyl, optionally substituted phenyl, optionally substituted phenoxy,
$R_F^2$ is hydrogen or $(C_1-C_4)$alkyl,
$R_F^3$ is hydrogen, $(C_1-C_8)$alkyl, $(C_2-C_4)$alkenyl, $(C_2-C_4)$alkynyl, or aryl, where each of the aforementioned carbon-containing radicals is unsubstituted or substituted by one or more, preferably up to three identical or different radicals from the group consisting of halogen and alkoxy; or salts thereof,
preferably compounds in which
$X_F$ is CH,
$n_F$ is an integer from 0 to 2,
$R_F^1$ is halogen, $(C_1-C_4)$alkyl, $(C_1-C_4)$haloalkyl, $(C_1-C_4)$alkoxy, $(C_1-C_4)$haloalkoxy,
$R_F^2$ is hydrogen or $(C_1-C_4)$alkyl,
$R_F^3$ is hydrogen, $(C_1-C_8)$alkyl, $(C_2-C_4)$alkenyl, $(C_2-C_4)$alkynyl, or aryl, where each of the aforementioned carbon-containing radicals is unsubstituted or substituted by one or more, preferably up to three identical or different radicals from the group consisting of halogen and alkoxy; or salts thereof.
S9) Active ingredients from the class of the 3-(5-tetrazolylcarbonyl)-2-quinolones (S9), e.g. 1,2-dihydro-4-hydroxy-1-ethyl-3-(5-tetrazolylcarbonyl)-2-quinolone (CAS reg. no.: 219479-18-2), 1,2-dihydro-4-hydroxy-1-methyl-3-(5-tetrazolylcarbonyl)-2-quinolone (CAS reg. no.: 95855-00-8), as described in WO-A-1999/000020.
S10) Compounds of the formulae (S10$^a$) or (S10$^b$) as described in WO-A-2007/023719 and WO-A-2007/023764

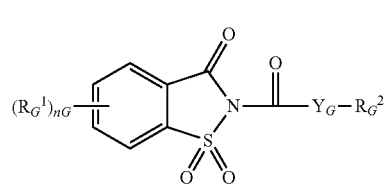
(S10$^a$)

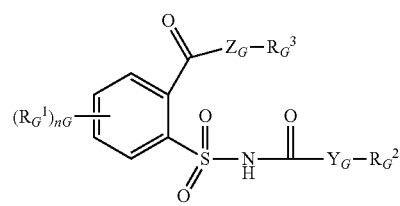
(S10$^b$)

in which
$R_G^1$ is halogen, $(C_1-C_4)$alkyl, methoxy, nitro, cyano, $CF_3$, $OCF_3$,
$Y_G$, $Z_G$ are each independently O or S,
$n_G$ is an integer from 0 to 4,
$R_G^2$ is $(C_1-C_{16})$alkyl, $(C_2-C_6)$alkenyl, $(C_3-C_6)$cycloalkyl, aryl; benzyl, halobenzyl,
$R_G^3$ is hydrogen or $(C_1-C_6)$alkyl.
S11) Active ingredients of the oxyimino compound type (S11), which are known as seed-dressing compositions, for example "oxabetrinil" ((Z)-1,3-dioxolan-2-yl-methoxyimino(phenyl)acetonitrile) (S11-1), which is known as a seed-dressing safener for millet/sorghum, against damage by metolachlor, "fluxofenim" (1-(4-chlorophenyl)-2,2,2-trifluoro-1-ethanone O-(1,3-dioxolan-2-ylmethyl)oxime) (S11-2), which is known as a seed-dressing safener for millet/sorghum against damage by metolachlor, and "cyometrinil" or "CGA-43089" ((Z)-cyanomethoxyimino(phenyl)acetonitrile) (S11-3), which is known as a seed-dressing safener for millet/sorghum against damage by metolachlor.
S12) Active ingredients from the class of the isothiochromanones (S12), for example methyl[(3-oxo-1H-2-benzothiopyran-4(3H)-ylidene)methoxy]acetate (CAS reg. no. 205121-04-6) (S12-1) and related compounds from WO-A-1998/13361.
S13) One or more compounds from group (S13): "naphthalic anhydride" (1,8-naphthalenedicarboxylic anhydride) (S13-1), which is known as a seed-dressing safener for corn against damage by thiocarbamate herbicides, "fenclorim" (4,6-dichloro-2-phenylpyrimidine) (S13-2), which is known as a safener for pretilachlor in sown rice, "flurazole" (benzyl 2-chloro-4-trifluoromethyl-1,3-thiazole-5-carboxylate) (S13-3), which is known as a seed-dressing safener for millet/sorghum against damage by alachlor and metolachlor, "CL 304415" (CAS reg. no. 31541-57-8) (4-carboxy-3,4-dihydro-2H-1-benzopyran-4-acetic acid) (S13-4) from American Cyanamid, which is known as a safener for corn against damage by imidazolinones, "MG 191" (CAS reg. no. 96420-72-3) (2-dichloromethyl-2-methyl-1,3-dioxolane) (S13-5) from Nitrokemia, which is known as safener for corn, "MG-838" (CAS reg. no. 133993-74-5) (2-propenyl 1-oxa-4-azaspiro[4.5]decane-4-carbodithioate) (S13-6) from Nitrokemia, "disulfoton" (O,O-diethyl S-2-ethylthioethyl phosphorodithioate) (S13-7), "dietholate" (O,O-diethyl O-phenylphosphorothioate) (S13-8), "mephenate" (4-chlorophenyl methylcarbamate) (S13-9).

S14) Active ingredients which, in addition to herbicidal action against harmful plants, also have safener action on crop plants such as rice, for example "dimepiperate" or "MY-93" (S-1-methyl-1-phenylethylpiperidine-1-carbothioate), which is known as a safener for rice against damage by the herbicide molinate, "daimuron" or "SK 23" (1-(1-methyl-1-phenylethyl)-3-p-tolylurea), which is known as a safener for rice against damage by the herbicide imazosulfuron, "cumyluron"="JC-940" (3-(2-chlorophenylmethyl)-1-(1-methyl-1-phenylethyl)urea, see JP-A-60087254), which is known as a safener for rice against damage by some herbicides, "methoxyphenone" or "NK 049" (3,3'-dimethyl-4-methoxybenzophenone), which is known as a safener for rice against damage by some herbicides, "CSB" (1-bromo-4-(chloromethylsulfonyl)benzene) from Kumiai, (CAS reg. no. 54091-06-4), which is known as a safener against damage by some herbicides in rice.

S15) Compounds of the formula (S15) or tautomers thereof as described in WO-A-2008/131861 and WO-A-2008/131860

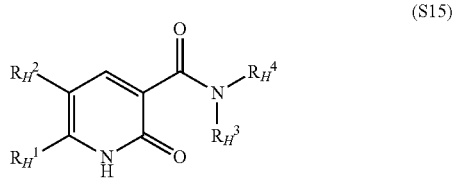

(S15)

in which $R_H^1$ is a $(C_1-C_6)$haloalkyl radical and $R_H^2$ is hydrogen or halogen and $R_H^3$, $R_H^4$ are each independently hydrogen, $(C_1-C_{16})$alkyl, $(C_2-C_{16})$alkenyl or $(C_2-C_{16})$alkynyl, where each of the latter 3 radicals is unsubstituted or substituted by one or more radicals from the group of halogen, hydroxy, cyano, $(C_1-C_4)$alkoxy, $(C_1-C_4)$haloalkoxy, $(C_1-C_4)$alkylthio, $(C_1-C_4)$alkylamino, di[$(C_1-C_4)$alkyl]amino, [$(C_1-C_4)$alkoxy]carbonyl, [$(C_1-C_4)$haloalkoxy]carbonyl, $(C_3-C_6)$cycloalkyl which is unsubstituted or substituted, phenyl which is unsubstituted or substituted, and heterocyclyl which is unsubstituted or substituted, or $(C_3-C_6)$cycloalkyl, $(C_4-C_6)$cycloalkenyl, $(C_3-C_6)$cycloalkyl which is fused on one side of the ring to a 4 to 6-membered saturated or unsaturated carbocyclic ring, or $(C_4-C_6)$cycloalkenyl which is fused on one side of the ring to a 4 to 6-membered saturated or unsaturated carbocyclic ring, where each of the latter 4 radicals is unsubstituted or substituted by one or more radicals from the group of halogen, hydroxy, cyano, (C1-C4)alkyl, (C1-C4)haloalkyl, (C1-C4)alkoxy, (C1-C4)haloalkoxy, (C1-C4)alkylthio, (C1-C4)alkylamino, di[(C1-C4)alkyl]amino, [(C1-C4)alkoxy]carbonyl, [(C1-C4)haloalkoxy]-carbonyl, (C3-C6)cycloalkyl which is unsubstituted or substituted, phenyl which is unsubstituted or substituted, and heterocyclyl which is unsubstituted or substituted, or $R_H^3$ is $(C_1-C_4)$alkoxy, $(C_2-C_4)$alkenyloxy, $(C_2-C_6)$alkynyloxy or $(C_2-C_4)$haloalkoxy and $R_H^4$ is hydrogen or $(C_1-C_4)$alkyl or $R_H^3$ and $R_H^4$ together with the directly bonded nitrogen atom form a four- to eight-membered heterocyclic ring which, as well as the nitrogen atom, may also contain further ring heteroatoms, preferably up to two further ring heteroatoms from the group of N, O and S, and which is unsubstituted or substituted by one or more radicals from the group of halogen, cyano, nitro, $(C_1-C_4)$alkyl, $(C_1-C_4)$haloalkyl, $(C_1-C_4)$alkoxy, $(C_1-C_4)$haloalkoxy and $(C_1-C_4)$alkylthio.

S16) Active ingredients which are used primarily as herbicides but also have safener action on crop plants, for example (2,4-dichlorophenoxy)acetic acid (2,4-D), (4-chlorophenoxy)acetic acid, (R,S)-2-(4-chloro-o-tolyloxy)propionic acid (mecoprop), 4-(2,4-dichlorophenoxy)butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (dicamba), 1-(ethoxycarbonyl)ethyl 3,6-dichloro-2-methoxybenzoate (lactidichlor-ethyl).

Substances which influence plant maturity:

Combination partners usable for the derivatives of (1-cyanocyclopropyl)phenylphosphinic acid or esters thereof, of the formula (I), and/or salts thereof, of the formula (II), in mixture formulations or in tankmixes are, for example, known active ingredients based on inhibition of, for example, 1-aminocyclopropane-1-carboxylate synthase, 1-aminocyclopropane-1-carboxylate oxidase and the ethylene receptors, for example ETR1, ETR2, ERS1, ERS2 or EIN4, as described, for example, in Biotechn. Adv. 2006, 24, 357-367; Bot. Bull. Acad. Sin. 199, 40, 1-7 or Plant Growth Reg. 1993, 13, 41-46 and literature cited therein.

Examples of known substances which influence plant maturity and can be combined with the derivatives of (1-cyanocyclopropyl)phenylphosphinic acid or esters thereof, of the formula (I), and/or salts thereof, of the formula (II), include the active ingredients which follow (the compounds are designated by the "common name" according to the International Organization for Standardization (ISO) or by the chemical name or by the code number) and always encompass all use forms, such as acids, salts, esters and isomers, such as stereoisomers and optical isomers. In this list, one or else, in some cases, more than one application form is mentioned by way of example:

rhizobitoxine, 2-aminoethoxyvinylglycine (AVG), methoxyvinylglycine (MVG), vinylglycine, aminooxyacetic acid, sinefungin, S-adenosylhomocysteine, 2-keto-4-methyl thiobutyrate, 2-(methoxy)-2-oxoethyl(isopropylidene)aminooxyacetate, 2-(hexyloxy)-2-oxoethyl(isopropylidene)aminooxyacetate, 2-(isopropyloxy)-2-oxoethyl(cyclohexylidene)aminooxyacetate, putrescine, spermidine, spermine, 1,8-diamino-4-aminoethyloctane, L-canaline, daminozide, methyl 1-aminocyclopropyl-1-carboxylate, N-methyl-1-aminocyclopropyl-1-carboxylic acid, 1-aminocyclopropyl-1-carboxamide, substituted 1-aminocyclopropyl-1-carboxylic acid derivatives as described in DE3335514, EP30287, DE2906507 or U.S. Pat. No. 5,123,951, 1-aminocyclopropyl-1-hydroxamic acid, 1-methylcyclopropene, 3-methylcyclopropene, 1-ethylcyclopropene, 1-n-propylcyclopropene, 1-cyclopropenylmethanol, carvone, eugenol Herbicides or plant growth regulators:

Combination partners usable for (1-cyanocyclopropyl) phenylphosphinic acid or esters thereof, of the formula (I), and/or salts thereof, of the formula (II), in mixture formulations or in tankmixes are, for example, known active ingredients based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoenesaturase, photosystem I, photosystem II, protoporphyrinogen oxidase, gibberellin biosynthesis, as described, for example, in Weed Research 26 (1986) 441-445 or "The Pesticide Manual", 14th edition, The British Crop Protection Council and the Royal Soc. of Chemistry, 2006 and literature cited therein.

Examples of known herbicides or plant growth regulators which can be combined with the derivatives of (1-cyanocyclopropyl)phenylphosphinic acid or esters thereof, of the formula (I), and/or salts thereof, of the formula (II), include the active ingredients which follow (the compounds are designated by the "common name" according to the International Organization for Standardization (ISO) or by the chemical name or by the code number) and always encompass all use forms, such as acids, salts, esters and isomers, such as stereoisomers and optical isomers. In this list, one or else, in some cases, more than one application form is mentioned by way of example:

acetochlor, acibenzolar, acibenzolar-S-methyl, acifluorfen, acifluorfen-sodium, aclonifen, alachlor, allidochlor, alloxydim, alloxydim-sodium, ametryne, amicarbazone, amidochlor, amidosulfuron, aminocyclopyrachlor, aminopyralid, amitrole, ammonium sulfamate, ancymidol, anilofos, asulam, atrazine, azafenidin, azimsulfuron, aziprotryne, beflubutamid, benazolin, benazolin-ethyl, bencarbazone, benfluralin, benfuresate, bensulide, bensulfuron, bensulfuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlortoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dimefuron, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl] phenyl]ethanesulfonamide, F-7967, i.e. 3-[7-chloro-5-fluoro-2-(trifluoromethyl)-1H-benzimidazol-4-yl]-1-methyl-6-(trifluoromethyppyrimidine-2,4(1H,3H)dione, fenoprop, fenoxaprop, fenoxaprop-P, fenoxaprop-ethyl, fenoxaprop-P-ethyl, fenoxasulfone, fentrazamide, fenuron, flamprop, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, flurochloridone, fluroxypyr, fluroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e. O-(2,4-dimethyl-6-nitrophenyl) O-ethyl isopropylphosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl) ethyl (2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indoleacetic acid (IAA), 4-indol-3-ylbutyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulfuron, metsulfuron-methyl, molinate, monalide, monocarbamide, monocarbamide dihydrogensulfate, monolinuron, monosulfuron, monosulfuron ester, monuron, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulfuron, nipyraclofen, nitralin, nitrofen, nitrophenolate-sodium (isomer mixture), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, SN-106279, i.e. methyl(2R)-2-({7-[2-chloro-4-(trifluoromethyl)phenoxy]-2-naphthyl}oxy)propanoate, sulcotrione, sulfallate (CDEC), sulfentrazone, sulfometuron, sulfometuron-methyl, sulfosate (glyphosate-trimesium), sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryne, thenylchlor, thiafluamide, thiazafluron, thiazopyr, thidiazimin, thidiazuron, thiencarbazone, thiencarbazone-methyl, thifensulfuron, thifensulfuron-methyl, thiobencarb, tiocarbazil, topramezone, tralkoxydim, triallate, triasulfuron, triaziflam, triazofenamide, tribenuron, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, and the following compounds:

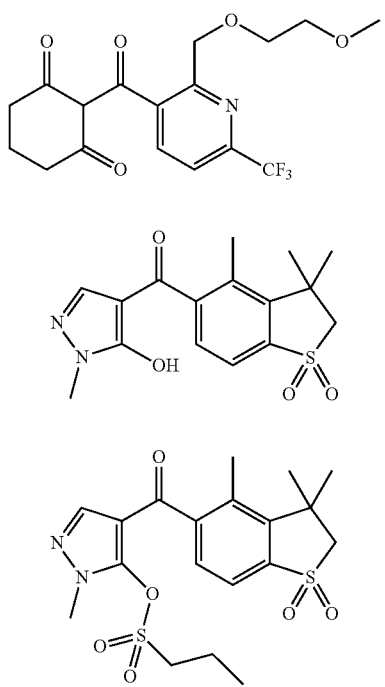

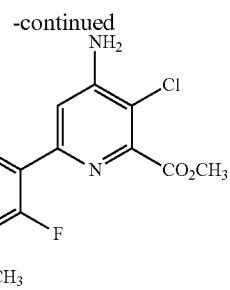

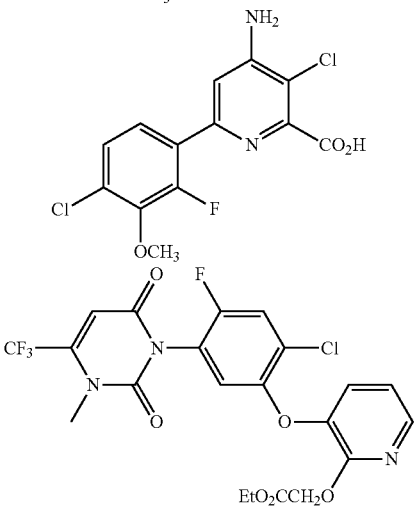

The invention is to be illustrated by the biological examples which follow, but without restricting it thereto.

BIOLOGICAL EXAMPLES

Seeds of monocotyledonous and dicotyledonous crop plants were placed in sandy loam in wood-fiber pots, covered with soil and cultivated in a greenhouse under good growth conditions. The test plants were treated at the early leaf stage (BBCH10-BBCH13). To ensure uniform water supply before commencement of stress, the potted plants were supplied with the maximum amount of water immediately beforehand by dam irrigation and, after application, transferred in plastic inserts in order to prevent subsequent, excessively rapid drying. The inventive compounds, formulated in the form of wettable powders (WP), wettable granules (WG), suspension concentrates (SC) or emulsion concentrates (EC), were sprayed onto the green parts of the plants as an aqueous suspension at an equivalent water application rate of 600 I/ha with addition of 0.2% wetting agent (agrotin). Substance application was followed immediately by stress treatment of the plants (cold or drought stress). For cold stress treatment, the plants are kept under the following controlled conditions:
"day": 12 hours with illumination at 8° C.
"night": 12 hours without illumination at 1° C.
Drought stress is induced by gradual drying out under the following conditions:
"day": 14 hours with illumination at 26° C.
"night": 10 hours without illumination at 18° C.
The duration of the respective stress phases was guided mainly by the state of the untreated, stressed control plants and thus varied from crop to crop. It was ended (by re-irrigating or transfer to a greenhouse with good growth conditions) as soon as irreversible damage was observed on the untreated, stressed control plants. In the case of dicotyledonous crops, for example oilseed rape and soya, the duration of the drought stress phase varied between 3 and 5 days, in the case of monocotyledonous crops, for example wheat, barley or corn, between 6 and 10 days. The duration of the cold stress phase varied between 12 and 14 days.

The end of the stress phase was followed by an approx. 5-7-day recovery phase, during which the plants were once again kept under good growth conditions in a greenhouse. In order to rule out any influence of the effects observed by any fungicidal action of the test compounds, it was additionally ensured that the tests proceed without fungal infection and without infection pressure.

After the recovery phase had ended, the intensities of damage were rated in visual comparison to untreated, unstressed controls of the same age (in the case of drought stress) or the same growth stage (in the case of cold stress). The intensity of damage was first assessed as a percentage (100%=plants have died, 0%=like control plants). These values were then used to calculate the efficacy of the test compounds (=percentage reduction in the intensity of damage as a result of substance application) by the following formula:

$$EF = \frac{(DV_{us} - DV_{ts}) \times 100}{DV_{us}}$$

EF: efficacy (%)

$DV_{us}$: damage value of the untreated, stressed control $DV_{ts}$: damage value of the plants treated with test compound Tables A.1, A.2 and A.3 show the efficacies of selected inventive compounds of the formula (I) and of the formula (II) on different crop plants (BRSNS=*Brassica napus* (A.1;) TRZAS=*Triticum aestivum* (A.2); ZEAMX=*Zea mays* (A.3) under drought stress.

The values stated each represent mean values from three results of the same test. The numbering corresponds to the numbering shown in tables 2 and 3.

TABLE A.1

| No. | Compound | Dosage | Unit | EF (BRSNS) |
|---|---|---|---|---|
| 1 | 2-2 | 25 | g/ha | >5 |
| 2 | 2-3 | 25 | g/ha | >5 |
| 3 | 2-16 | 250 | g/ha | >5 |
| 4 | 2-17 | 250 | g/ha | >5 |
| 5 | 2-18 | 25 | g/ha | >5 |
| 6 | 2-19 | 25 | g/ha | >5 |
| 7 | 2-34 | 25 | g/ha | >5 |
| 8 | 2-37 | 25 | g/ha | >5 |
| 9 | 2-111 | 25 | g/ha | >5 |
| 10 | 2-130 | 25 | g/ha | >5 |
| 11 | 2-132 | 25 | g/ha | >5 |
| 12 | 2-134 | 250 | g/ha | >5 |
| 13 | 2-135 | 25 | g/ha | >5 |
| 14 | 2-141 | 25 | g/ha | >5 |
| 15 | 2-142 | 25 | g/ha | >5 |
| 16 | 2-155 | 25 | g/ha | >5 |
| 17 | 2-158 | 25 | g/ha | >5 |
| 18 | 2-159 | 25 | g/ha | >5 |
| 19 | 3-1 | 25 | g/ha | >5 |

TABLE A.2

| No. | Compound | Dosage | Unit | EF (TRZAS) |
|---|---|---|---|---|
| 1 | 2-2 | 25 | g/ha | >5 |
| 2 | 2-135 | 25 | g/ha | >5 |
| 3 | 2-141 | 250 | g/ha | >5 |

TABLE A.3

| No. | Compound | Dosage | Unit | EF (ZEAMX) |
|---|---|---|---|---|
| 1 | 2-130 | 25 | g/ha | >5 |
| 2 | 2-155 | 25 | g/ha | >5 |
| 3 | 2-158 | 250 | g/ha | >5 |

Similar results were also achieved with further compounds of the formula (I), or of the formula (II), also in the case of application to different plant species.

The invention claimed is:

1. A method for increasing tolerance in plants to abiotic stress, comprising:
applying an effective amount of a derivative of (1-cyanocyclopropyl)phenylphosphinic acid of the formula (I), or an ester or salt thereof, to the plants;
wherein formula (I) is:

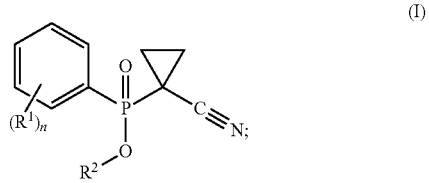

where:
$R^1$ is:
halogen; or
a branched or unbranched alkyl, cycloalkyl, alkenyl, alkynyl, aryl, arylalkyl, heteroaryl, heteroarylalkyl, alkoxyalkyl, hydroxyalkyl, alkoxyalkenyl, alkylthio, haloalkylthio, alkylsulfinyl, alkylsulfonyl, haloalkyl, alkoxy, haloalkoxy, carboxyl, alkoxycarbonyl, aminocarbonyl which is optionally mono- or disubstituted; or
cyano, amino, or nitro;
$R^2$ is hydrogen, or a branched or unbranched alkyl, cycloalkyl, cycloalkylalkyl, alkenyl, alkenylalkyl, alkynyl, alkynylalkyl, aryl, arylalkyl, heteroaryl, heteroarylalkyl, alkoxyalkyl, hydroxyalkyl, alkoxyalkenyl, hydroxyalkenyl, alkylthioalkyl, haloalkyl, alkylaminoalkyl, bisalkylaminoallyl, or cycloalkylaminoalkyl; and
n is 0, 1, 2, 3, 4, or 5.

2. The method of claim 1, wherein:
$R^1$ is a halogen, or a branched or unbranched alkyl, cycloalkyl, alkenyl, alkynyl, aryl, alkoxyalkyl, alkylthio, haloalkyl, alkoxy, carboxyl, or alkoxycarbonyl;
$R^2$ is hydrogen, or a branched or unbranched alkyl, cycloalkyl, alkenyl, alkynyl, arylalkyl, heteroaryl, heteroarylalkyl, alkoxyalkyl, hydroxyalkyl, hydroxyalkenyl, or haloalkyl; and
n is 0, 1, 2, 3, 4, 5.

3. The method of claim 1, wherein:

$R^1$ is a halogen, or a branched or unbranched $(C_1-C_6)$-alkyl, $(C_3-C_7)$-cycloalkyl, $(C_2-C_4)$-alkenyl, $(C_1-C_4)$-alkynyl, $(C_1-C_4)$-alkoxy-$(C_1-C_4)$-alkyl, $(C_1-C_4)$-alkylthio, halo-$(C_2-C_4)$-alkyl, $(C_1-C_4)$-alkoxy, carboxyl, or $(C_1-C_4)$-alkoxycarbonyl;

$R^2$ is hydrogen, or a branched or unbranched $(C_1-C_6)$-alkyl, $(C_3-C_7)$-cycloalkyl, $(C_2-C_6)$-alkenyl, $(C_2-C_6)$-alkynyl, $(C_1-C_4)$-alkoxy-$(C_1-C_4)$-alkyl, or halo-$(C_1-C_6)$-alkyl; and n is 0, 1, 2 or 3.

4. The method of claim 1;

wherein an effective amount of a salt of formula (II), of the derivative of formula (I), is applied to the plants;

wherein formula (II) is:

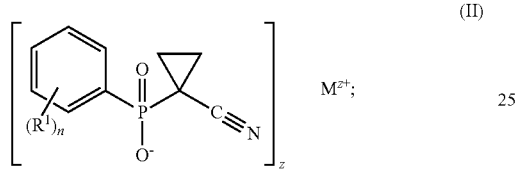

(II)

where:
the cation (M) is
(a) an ion of an alkali metal; or
(b) an ion of an alkaline earth metal; or
(c) an ion of an transition metal; or
(d) an ammonium ion in which one, two, three or all four hydrogen atoms are optionally replaced by identical or different radicals from the group of $(C_1-C_4)$-alkyl, hydroxy-$(C_1-C_4)$-alkyl, $(C_3-C_6)$-cycloalkyl, $(C_1-C_4)$-alkoxy-$(C_1-C_4)$-alkyl, hydroxy-$(C_1-C_4)$-alkoxy-$(C_1-C_4)$-alkyl, $(C_1-C_6)$-mercaptoalkyl, phenyl or benzyl, where the aforementioned radicals are optionally substituted by one or more identical or different radicals from the group consisting of halogen, nitro, cyano, azido, $(C_1-C_6)$-alkyl, $(C_1-C_6)$-haloalkyl, $(C_3-C_6)$-cycloalkyl, $(C_1-C_6)$-alkoxy, $(C_1-C_6)$-haloalkoxy and phenyl, and where in each case two substituents on the nitrogen atom together optionally form an unsubstituted or substituted ring; or
(e) a phosphonium ion; or
(f) a sulfonium ion or sulfoxonium ion; or
(g) an oxonium ion; or
(h) an optionally singly or multiply fused, and/or $(C_1-C_4)$-alkyl-substituted, saturated or unsaturated or aromatic, N-containing heterocyclic ionic compound having 1-10 carbon atoms in the ring system; and
z is 1, 2, or 3.

5. The method of claim 1;

wherein an effective amount of a salt of formula (II), of the derivative of formula (I), is applied to the plants;

wherein formula (II) is:

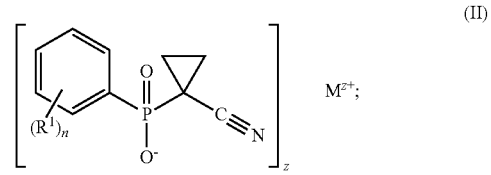

(II)

where:
the cation (M) is
(a) an ion of an alkali metal; or
(b) an ion of an alkaline earth metal; or
(c) an ion of an transition metal; or
(d) an ammonium ion in which one, two, three or all four hydrogen atoms are optionally replaced by identical or different radicals from the group of $(C_1-C_4)$-alkyl, hydroxy-$(C_1-C_4)$-alkyl, $(C_3-C_4)$-cycloalkyl, $(C_1-C_2)$-alkoxy-$(C_1-C_2)$-alkyl, hydroxy-$(C_1-C_2)$-alkoxy-$(C_1-C_2)$-alkyl, $(C_1-C_2)$-mercaptoalkyl, phenyl or benzyl, where the aforementioned radicals are optionally substituted by one or more identical or different radicals from the group consisting of halogen, nitro, cyano, azido, $(C_1-C_2)$-alkyl, $(C_1-C_2)$-haloalkl, $(C_3-C_4)$-cycloalkyl, $(C_1-C_2)$-alkoxy, $(C_1-C_2)$-haloalkoxy and phenyl, and where in each case two substituents on the nitrogen atom together optionally form an unsubstituted or substituted ring; or
(e) a quaternary phosphonium ion; or
(f) a tertiary sulfonium ion or sulfoxonium ion; or
(g) a tertiary oxonium ion; or
(h) a cation selected from the group consisting of pyridine, quinoline, 2-methylpyridine, 3-methylpyridine, 4-methylpyridine, 2,4-dimethylpyridine, 2,5-dimethylpyridine, 2,6-dimethylpyridine, 5-ethyl-2-methylpyridine, piperidine, pyrrolidine, morpholine, thiomorpholine, pyrrole, imidazole, 1,5-diazabicyclo[4.3.0]non-5-ene (DBN), and 1,8-diazabicyclo[5.4.0]undec-7-ene (DBU); and
z is 1, 2 or 3.

6. The method of claim 1;

wherein the abiotic stress conditions correspond to one or more conditions selected from the group consisting of drought, aridity and lack of water, cold and hot conditions, osmotic stress, waterlogging, elevated soil salinity, elevated exposure to minerals, ozone conditions, strong light conditions, limited availability of nitrogen nutrients, limited availability of phosphorus nutrients, and shade avoidance.

7. The method of claim 1;

wherein the plants are selected from the group consisting of useful plants, ornamental plants, turfgrass types, and trees; and wherein the application is to the plants, to the seed thereof, or to the area on which the plants grow.

8. The method as claimed in claim 1;

wherein the resistance of the plants thus treated to abiotic stress is increased by at least 3% compared to untreated plants under otherwise identical physiological conditions.

9. The method of claim 4, wherein:
(a) the ion of the alkali metal is lithium, sodium, or potassium;
(b) the ion of the alkaline earth metal is calcium or magnesium;
(c) the ion of the transition metal is manganese, copper, zinc, or iron;
(f) the sulfonium ion or sulfoxonium ion is tri-$((C_1\text{-}C_4)$-alkyl)sulfonium or tri-$((C_1\text{-}C_4)$-alkyl)sulfoxonium; and
(g) the oxonium ion is tri-$((C_1\text{-}C_4)$-alkyl)oxonium.

10. The method of claim 5, wherein:
(a) the ion of the alkali metal is lithium, sodium, or potassium;
(b) the ion of the alkaline earth metal is calcium or magnesium;
(c) the ion of the transition metal is manganese, copper, zinc, or iron;
(e) the quaternary phosphonium ion is a tetra-$((C_1\text{-}C_4)$-alkyl)phosphonium or tetraphenylphosphonium, where the $(C_1\text{-}C_4)$-alkyl radicals and the phenyl radicals are optionally mono- or polysubstituted by identical or different radicals selected from the group consisting of halogen, $(C_1\text{-}C_2)$-alkyl, $(C_1\text{-}C_2)$-haloalkyl, $(C_3\text{-}C_4)$-cycloalkyl, $(C_1\text{-}C_2)$-alkoxy and $(C_1\text{-}C_2)$-haloalkoxy;
(f) the tertiary sulfonium ion or sulfoxonium ion is a tri-$((C_1\text{-}C_4)$-alkyl)sulfonium or triphenylsulfonium, where the $(C_1\text{-}C_4)$-alkyl radicals and the phenyl radicals are optionally mono- or polysubstituted by identical or different radicals selected from the group consisting of halogen, $(C_1\text{-}C_2)$-alkyl, $(C_1\text{-}C_2)$-haloalkyl, $(C_3\text{-}C_4)$-cycloalkyl, $(C_1\text{-}C_2)$-alkoxy and $(C_1\text{-}C_2)$-haloalkoxy, or tri-$((C_1\text{-}C_4)$-alkyl)sulfoxonium; and
(g) the tertiary oxonium ion is a tri-$((C_1\text{-}C_4)$-alkyl)oxonium, where the $(C_1\text{-}C_4)$-alkyl radicals are optionally mono- or polysubstituted by identical or different radicals selected from the group consisting of halogen, $(C_1\text{-}C_2)$-alkyl, $(C_1\text{-}C_2)$-haloalkyl, $(C_3\text{-}C_4)$-cycloakl, $(C_1\text{-}C_2)$-alkoxy and $(C_1\text{-}C_2)$-haloalkoxy.

11. A method for increasing tolerance of genetically modified cultivars to abiotic stress, comprising:
applying an effective amount of a derivative of (1-cyanocyclopropyl)phenylphosphinic acid of the formula (I), and/or of one or more esters or salts thereof, to the genetically modified cultivars, to seed of the genetically modified cultivars, or to cultivation areas on which these cultivars grow;
wherein formula (I) is:

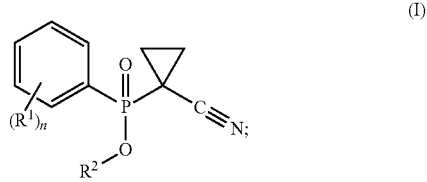

where:
$R^1$ is:
halogen; or
a branched or unbranched alkyl, cycloalkyl, alkenyl, alkynyl, aryl, arylalkyl, heteroaryl, heteroarylalkyl, alkoxyalkyl, hydroxyalkyl, alkoxyalkenyl, alkylthio, haloalkylthio, alkylsulfonyl, haloalkyl, alkoxy, haloalkoxy, carboxyl, alkoxycarbonyl, aminocarbonyl which is optionally mono- or disubstituted; or
cyano, amino, or nitro;
$R^2$ is hydrogen, or a branched or unbranched alkyl, cycloalkyl, cycloalkylalkyl, alkenyl, alkenylalkyl, alkynyl, alkynylalkyl, aryl, arylalkyl, heteroaryl, heteroarylalkyl, alkoxyalkyl, hydroxyalkyl, alkoxyalkenyl, hydroxyalkenyl, alkylthioalkyl, haloalkyl, alkylaminoalkyl, bisalkylaminoalkyl, or cycloalkylaminoalkyl; and
n is 0, 1, 2, 3, 4, or 5.

* * * * *